United States Patent

Kijima et al.

[11] Patent Number: 5,971,609
[45] Date of Patent: Oct. 26, 1999

[54] METHOD OF MEASURING THE DEW POINT OR FROST POINT OF A GAS HAVING LOW WATER CONTENT

[75] Inventors: Takahiko Kijima; Akira Makihara; Hiroshi Nakamura; Shigeru Kikuchi; Shigeki Hayashi, all of Osaka, Japan

[73] Assignee: Osaka Sanso Kogyo Ltd., Osaka, Japan

[21] Appl. No.: 08/817,139

[22] PCT Filed: Oct. 31, 1995

[86] PCT No.: PCT/JP95/02229

§ 371 Date: Apr. 9, 1997

§ 102(e) Date: Apr. 9, 1997

[87] PCT Pub. No.: WO96/13713

PCT Pub. Date: May 9, 1996

[30] Foreign Application Priority Data

Oct. 31, 1994 [JP] Japan ................................. 6-302620

[51] Int. Cl.[6] ................ G01N 25/68; G01N 21/47; G01N 21/55
[52] U.S. Cl. ................ 374/17; 374/20; 356/445; 73/29.01
[58] Field of Search ................ 374/20, 19, 18, 374/17, 16, 27, 28; 73/335.01, 29.01; 356/445

[56] References Cited

U.S. PATENT DOCUMENTS

| | | |
|---|---|---|
| 4,629,333 | 12/1986 | Dosoretz et al. ................ 374/20 |
| 4,946,288 | 8/1990 | Siska et al. ................ 374/20 |
| 5,022,045 | 6/1991 | Elliott ................ 374/20 |
| 5,052,818 | 10/1991 | Nishizawa et al. ................ 374/20 |
| 5,299,867 | 4/1994 | Buck ................ 374/20 |
| 5,482,371 | 1/1996 | Nishizawa et al. ................ 374/20 |

Primary Examiner—Diego Gutierrez
Attorney, Agent, or Firm—Roylance, Abrams, Berdo & Goodman, L.L.P

[57] ABSTRACT

A method of determining the dew point or frost point of a gas containing a very small amount of water uses an optical dew point meter having a reflector mirror the temperature of which can be varied from room temperature to any point of −80° C. or below, a device for contacting the reflector mirror with the gas to be measured, a light source for irradiating the reflector mirror with focused rays of light, and a detector for detecting the change in scattered light and/or reflected light due to the dew and/or frost condensed on the reflector mirror. The method gradually reduces the temperature of the reflector mirror, either before or while the reflector mirror and the gas contact, thereby condensing dew and/or frost on the reflector mirror. Following formation of dew and/or frost on the reflector mirror, the intensity of scattered light or reflected light is adjusted from a maximum value to a constant level, at a controlled temperature. The temperature at that constant level of light intensity is determined as the dew or frost point.

9 Claims, 23 Drawing Sheets

SCHEMATIC LAYOUT FOR GENERATION AND DILUTION OF STANDARD GAS OF LOW WATER CONTENT of a gas to be measured under the condition of an instantaneous equilibrium between the solid and vapor phases of water, thereby assuring that the measured dew point or frost point corresponds to the saturation temperature of the gas while, at the same time, the vapor pressure of the gas corresponds to the saturation vapor pressure of ice at that temperature.

METHOD OF MEASURING THE DEW POINT OR FROST POINT OF A GAS HAVING LOW WATER CONTENT

BACKGROUND OF THE INVENTION

The present invention enables the dew point or frost point of a gas to be measured under the condition of an instantaneous equilibrium between the solid and vapor phases of water, thereby assuring that the measured dew point or frost point corresponds to the saturation temperature of the gas while, at the same time, the vapor pressure of the gas corresponds to the saturation vapor pressure of ice at that temperature.

As has been pointed out in the references of many researchers, dictionaries and patents, it takes a very long time to measure dew points or frost points, particularly low dew points or frost points, and supercooling often takes place when the dew point or frost point to be measured is −100° C. or below.

As a result of many repeated experiments, the present inventors have discovered a method that is believed to be the most accurate way of dew point or frost point measurement that is practical enough to be implemented with an industrially useful dew point or frost point meter.

It has been known to determine the water content of a gas by measuring its dew or frost point (see, for example, U.S. Pat. No. 5,052,818). In that method, the gas to be measured is blown against a reflecting mirror cooled to −80° C. or below and the condensation of dew or frost on the reflecting mirror is detected by a sudden increase in scattered light and the water content of the gas is determined from the dew or frost point. However, later studies of the present inventors have shown that below −90° C., the amount of condensation of dew or frost on the reflector mirror is so small that the detector sometimes fails to achieve the correct sensing of the point where such dew or frost condensation has occurred. Even if dew or frost condensation can be sensed by the detector, one often cannot be sure whether the sensed point of dew or frost condensation reflects the correct dew or frost point. In addition, if a phenomenon called "supercooling" occurs, dew or frost will not be condensed at the temperature where dew or frost condensation would otherwise occur. In this case, too, one if unable to know for sure whether the measured point reflects the correct dew or frost point.

As a result of the extensive studies they conducted, the present inventors found that when the reflector mirror on which dew or frost formed was further held at a lower temperature until the formation of a solid phase of water in a suitable amount and when heating and cooling steps were taken, preferably through at least one cycle, such that the temperature was controlled to decrease from the point where the intensity of scattered light was at a maximum or from the point where the intensity of reflected light was at a minimum to the point where the intensity of scattered or reflected light was at a specified level, the temperature at that point could safely be considered as the temperature of dew or frost formation. The present invention has been accomplished on the basis of this finding.

SUMMARY OF THE INVENTION

This invention relates to a method of determining the dew point or frost point of a gas containing a very small amount of water using an optical dew point meter including a reflector mirror the temperature of which can be varied from room temperature to any point of down to −80° C. or below, a means of contacting said reflector mirror with the gas to be measured, a means of irradiating said reflector mirror with focused rays of light or with laser light, and a means of detecting the change in scattered light or the change in reflected light due to the dew or due to the frost condensed on said reflector mirror, said method comprising the steps of:

contacting said reflector mirror with the gas to be measured;

applying said focused rays of light or said laser light onto that part of the reflector mirror where it is contacted with said gas;

gradually reducing the temperature of said reflector mirror, either before or while said reflector mirror and said gas contact, thereby condensing dew or frost one said reflector mirror; and following the formation of dew or frost on said reflector mirror, adjusting the intensity of scattered light or reflected light from a maximum value to a constant level, at a controlled temperature and determining the temperature at that constant level of light intensity as the dew or frost point.

DETAILED DESCRIPTION OF THE INVENTION

The temperature of said reflector mirror is gradually reduced by cooling or elevated by heating said reflector mirror at a rate that is varied either stepwise or continuously generally along the curve represented by:

$$R(T)=R(T_o)[P'(T)/P'(T_o)]^n$$

where T: the temperature (K) of the reflector mirror;

$T_o$: any specific temperature (K) that can be selected from the range of from room temperature to the temperature of liquid nitrogen;

R(T): the cooling rate or the heating rate (K/min) at a selected temperature (K) of the reflector mirror;

P'(T): the derived function of the saturated vapor pressure of ice determined with the temperature (T) being taken as a variable;

$P'(T_o)$: a calculated value of the standard vapor pressure of water at the specific temperature $T_o$; and n: the value so selected as to provide a substantially constant signal-to-noise ratio of at least 2 in the measurement of the change in reflected light or of at least 2 in the measurement of the change in scattered light over a fixed temperature interval $\Delta T$.

To explain the theory of the invention, the concept of a so-called dew or frost point meter is described below with reference to FIG. 1.

Figure 1:
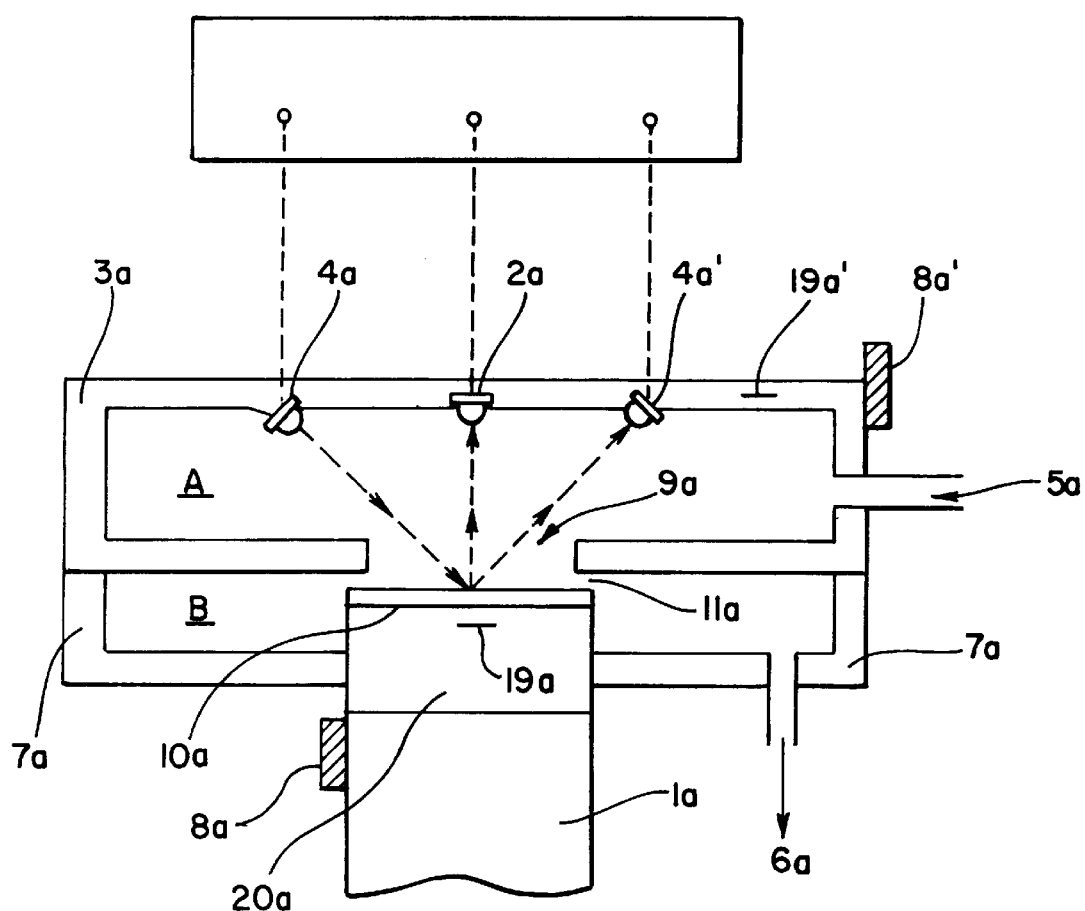
FIG. 1 shows the concept of a dew or frost point meter operating on the change in the intensity of scattered light or intensity of reflected light from a reflector mirror.

Indicated by 1a in FIG. 1 is a freeze generating portion; 8a is a heater; and 20a is a chill surface. Compartment A is enclosed with a wall 3a of a good heat conductor such as gold, silver, copper, aluminum, silicon, nickel or chromium. Indicated by 5a is an inlet for the gas to be measured. Compartment B is enclosed largely with a wall 7a and partly with a wall 3a, and a hole 9a is made in the compartment partition of compartments A and B. Indicated by 11a is a gap between a reflector mirror 10a and the partition of compartments A and B. At least part of the wall 7a enclosing compartment B is made of a poor heat conductor such as stainless steel, a copper-nickel alloy, glass, ceramics, and plastics (e.g. fluoro, polyimide and silicone resins) in order to insure against cooling of compartment A with the chill surface 20a. Indicated by 6a is a gas outlet. Indicated by 4a is a light source fitted with a condenser lens and is typically an LED emitting at a given wavelength. The light emitted from the source 4a and reflected by the reflector mirror 10 is picked up by maximal condensation with a photodetector 4a' fitted with a condenser lens. Any light that issues from the source 4a and scattered by the reflector mirror 10a is picked up by a photodetector 2a fitted with a condenser lens.

Frost point meters are generally of three types, a reflection type that uses the light source 4a and the detector 4a' for sensing reflected light, a scattering type that uses the light source 4a and the detector 2a for sensing scattered light, and a third type that detects both reflected and scattered light.

Figure 2:
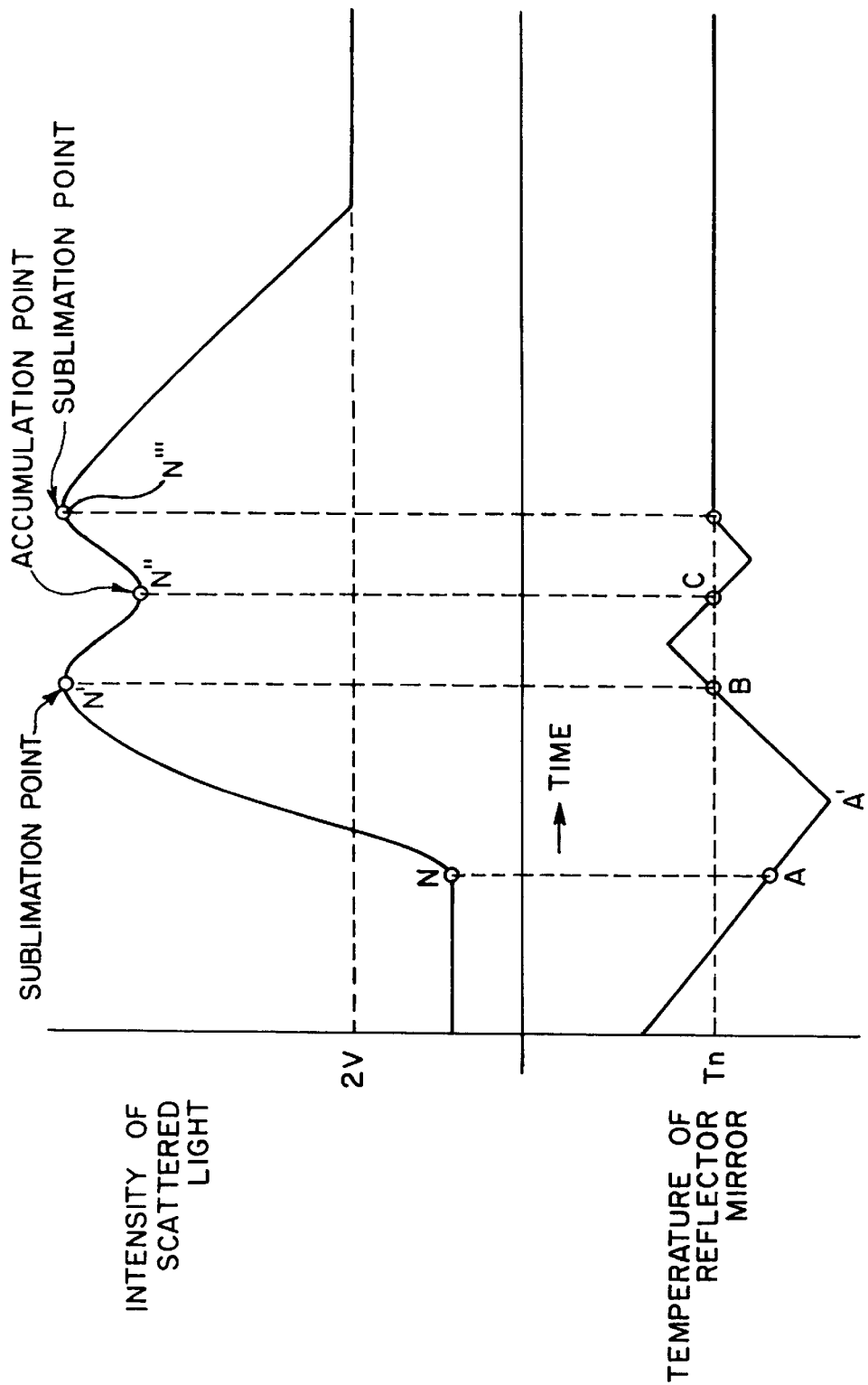
FIG. 2 is a graph showing the relationship between the temperature of the reflector mirror and the intensity of scattered light.
Figure 3:
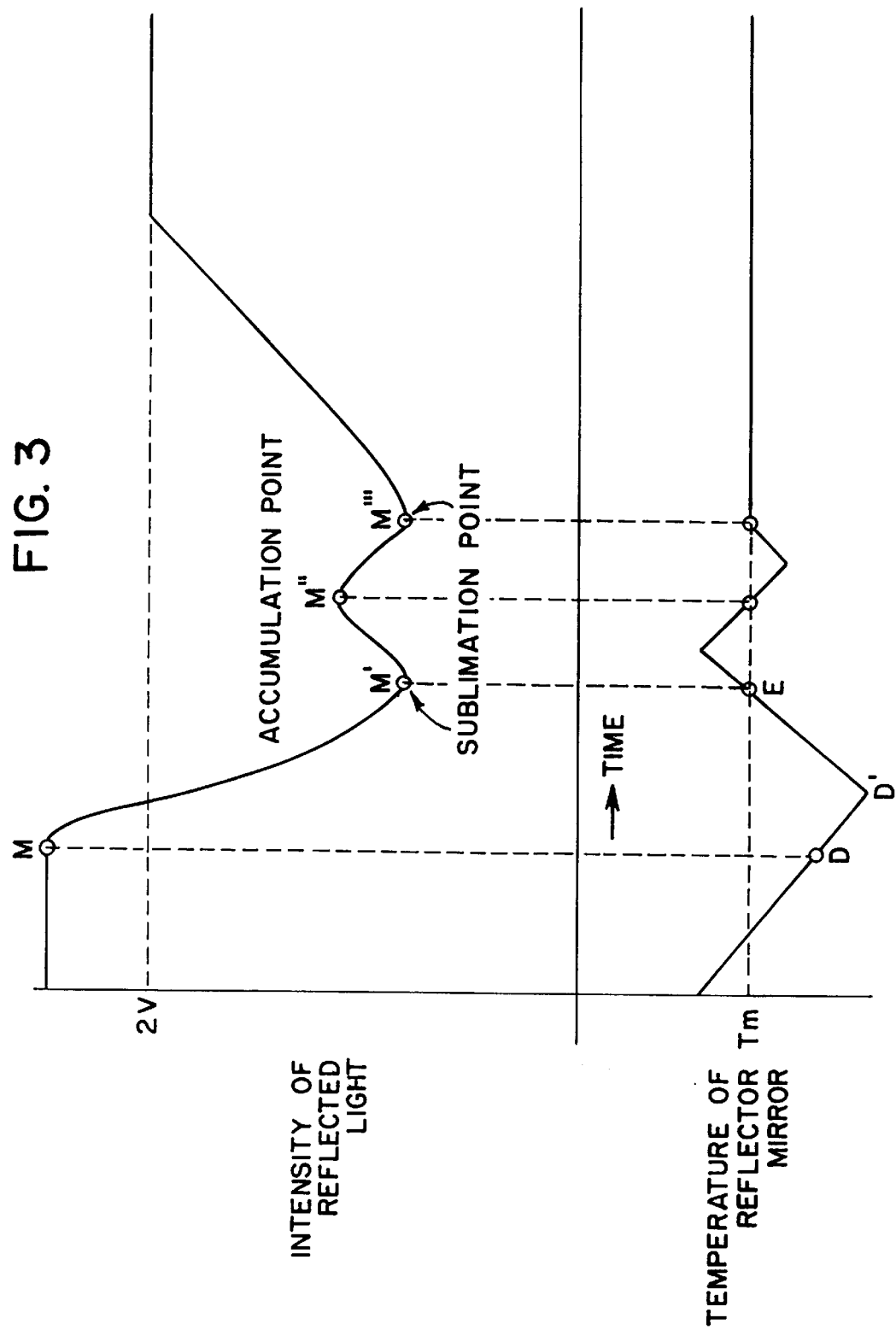
FIG. 3 is a graph showing the relationship between the temperature of the reflector mirror and the intensity of reflected light.

The measurement of the dew or frost point of a certain gas by means of the above-described apparatus will proceed as follows. A gas to be measured is introduced into compartment A through inlet 5a. Compartment A is held at a specified temperature by means of heater 8a' and a thermometer 19a'. The gas passes through the hole 9a and contacts the reflector mirror 10a to form dew or frost on it. The gas then passes through the gap 11a and leaves compartment B through outlet 6a. The reflector mirror is cooled or heated by the combination of freeze generator 1a and the heater 8a in accordance with a specified procedure with the temperature being monitored by means of a temperature sensor 19a inserted near the mirror 10a. As the reflector mirror is cooled, dew or frost forms on its surface and scatters the light from the source 4a, whereupon the intensity of the light picked up by the photodetector 2a will increase, as shown in FIG. 2. At point N in FIG. 2, the detector 2a senses that the intensity of scattered light starts to increase and the temperature of the reflector mirror (Tn) at that point is indicated by point A. The scattering of the light by the dew or frost that has formed on the mirror surface leads to a smaller intensity of the reflected light picked up by the photodetector 4a', as shown in FIG. 3. At point N', the detector senses that the intensity of reflected light starts to decrease and the temperature of the reflector mirror (Tn') at that point is indicated by point A'.

The principle of interest will now be described with reference to FIG. 2. First assume that the temperature of the reflector mirror is lowered until dew or frost forms at point A. However, a certain time is required to insure that the rise of the intensity of scattered light is by no means due to noise; hence, the cooling of the reflector mirror is continued until point A' is reached. The correct temperature at point A is determined by reverse calculation from point A'. However, the reflector mirror has been supercooled at point A, so it does not indicate the dew or frost point at equilibrium. Ice starts to grow at point N corresponding to point A and the intensity of scattered light increases. At point A', a step is taken to elevate the temperature of the reflector mirror but due to the heat capacity of the cell, the ice continues to grow but it eventually stops growing. Then, water starts to evaporate and the point at which the intensity of scattered light becomes maximal may well be determined as the point of sublimation N'.

On account of noise, the intensity of actual scattered light does not draw a simple parabolic curve but draws an undulated parabolic curve as in a record of seismic waves. A computer will not recognize a maximal intensity of scattered light until it exceeds the maximal point by a sufficient amount to be distinguishable from noise. However, the maximal point can be determined by calculations, so as long as the maximal point of the intensity of scattered light (i.e., the point of sublimation) N' is recognized, the temperature of the reflector mirror at that point (Tn corresponding to point B) may well be determined as the dew or frost point. The heart of the invention does not lie in determining the dew or frost point from the maximal point of the intensity of scattered light. The reflector mirror will be kept heated after the temperature of the reflector mirror has reached the point of sublimation (N' or B).

When the computer has recognized that the point for the maximal intensity of scattered light was reached, the reflector mirror is cooled again until the intensity of scattered light becomes minimal at point N". As in the case of a maximal value for the intensity of scattered light, noise will allow the computer to recognize the point for the minimal intensity of scattered light only when a short time has passed after the actual minimal point was reached. The point N" where the intensity of scattered light is minimal is the point of solidification of superposed layers.

Since the minimal point for the intensity of scattered light N" (i.e., the point of solidification of superposed layers) can be recognized in the same manner as in the case of recognizing the maximal point, the temperature of the reflector mirror (Tn=C) at that point may well be determined as the dew or frost point.

In the actual practice of the invention, the temperature of the reflector mirror is adjusted in such a way as to provide the maximal point for the intensity of scattered light N" (point of sublimation) again and, thereafter, an adjustment is made to a certain value, say, 2 V, and the temperature of the mirror is controlled to keep this constant voltage. The temperature at which the intensity of scattered light is held constant is determined as the dew or frost point. Needless to say, the adjustment to a constant voltage, say, 2 V, for determining the dew or frost point may be effected when the first occurrence of the sublimation point (N') has been recognized.

The same principle is further described with reference to FIG. 3. First assume that the temperature of the reflector mirror is lowered until dew or frost forms at point D. However, a certain time is required to insure that the decrease of the intensity of reflected light is by no means due to noise; hence, the cooling of the reflector mirror is continued until point D' is reached. The correct temperature at point D is determined by reverse calculation from point A'. However, the reflector mirror has been supercooled at point D, so it does not indicate the dew or frost point at equilibrium. Ice starts to grow at point M corresponding to point D and the intensity of reflected light decreases. At point D', a step is taken to elevate the temperature of the reflector mirror but due to the heat capacity of the cell, the ice continues to grow but it eventually stops growing. Then water starts to evaporate and the point at which the intensity of reflected light becomes minimal may well be determined as the point of sublimation M'.

On account of noise, the intensity of actual reflected light does not draw a simple parabolic curve but draws an undulated parabolic curve as in a record of seismic waves. A computer will not recognize a minimal intensity of reflected light until it exceeds the minimal point by a sufficient amount to be distinguishable from noise. However, the minimal point can be determined by calculations, so as long as the minimal point of the intensity of reflected light (i.e., the point of sublimation) M' is recognized, the temperature of the reflector mirror at that point (Tm corresponding to point E) may well be determined as the dew or frost point. The heart of the invention does not lie in determining the dew or frost point from the minimal point of the intensity of reflected light. The reflector mirror will be kept heated after the temperature of the reflector mirror has reached the point of sublimation (M' or E).

When the computer has recognized that the point for the minimal intensity of reflected light was reached, the reflector mirror is cooled again until the intensity of reflected light becomes maximal at point M". As in the case of a minimal value for the intensity of reflected light, noise will allow the computer to recognize the point for the maximal intensity of reflected light only when a short time has passed after the actual maximal point was reached. The point M" where the intensity of reflected light is maximal is the point of solidification of superposed layers.

Since the maximal point for the intensity of reflected light M" (i.e., the point of solidification of superposed layers) can be recognized in the same manner as in the case of recognizing the minimal point, the temperature of the reflector mirror (Tm=F) at that point may well be determined as the dew or frost point.

In the actual practice of the invention, the temperature of the reflector mirror is adjusted in such a way as to provide the minimal point for the intensity of reflected light M" (point of sublimation) again and, thereafter, an adjustment is made to a certain value, say, 2 V, and the temperature of the mirror is controlled to keep this constant voltage. The temperature at which the intensity of reflected light is held constant is determined as the dew or frost point. Needless to say, the adjustment to a constant voltage, say, 2 V, for determining the dew or frost point may be effected when the first occurrence of the sublimation point (M') has been recognized.

Profiles for the cooling and heated rates in the case under consideration are given below.

TABLE 1

| Cooling Rate | | |
|---|---|---|
| Temperature range (° C.→° C.) | | Cooling rate (° C./min) |
| 20 | −70 | 10.0 |
| −70 | −90 | 4.0 |
| −90 | −100 | 2.0 |
| −100 | −105 | 1.0 |
| −105 | −110 | 0.50 |
| −110 | −115 | 0.25 |
| −115 | −120 | 0.13 |
| −120 | −125 | 0.063 |
| −125 | −130 | 0.031 |
| −130 | −135 | 0.016 |

TABLE 2

| Heating Rate | | |
|---|---|---|
| Temperature range (° C.→° C.) | | Heating rate (° C./min) |
| −135 | −135 | 0.016 |
| −130 | −125 | 0.031 |
| −125 | −120 | 0.063 |
| −120 | −115 | 0.13 |
| −115 | −110 | 0.25 |
| −110 | −105 | 0.50 |
| −105 | −100 | 1.0 |
| −100 | −90 | 2.0 |
| −90 | −70 | 4.0 |
| −70 | 30 | 10.0 |

Equation (1) is a formula for a curve. The lower the temperature, the slower the heating and cooling rates. In the case under consideration, the rate of cooling from 20° C. to −70° C. is 10.0° C./min whereas the rate of cooling from −130° C. to −135° C. is 0.016° C./min. If it is assumed that cooling or heating is conducted following the curved path represented by Equation (1), the heating or cooling rate must be slowed down at decreasing temperature and to achieve this, performing a fully computer-aided control is ideal. However, this approach is not economical.

The common practice is to lower the cooling or heating rate stepwise as shown in the above Tables. The cooling or heating rate is varied for every decrement of 5° C.

Varying the heating or cooling rate stepwise following the curved path represented by Equation (1) means substantially the same as illustrated by Tables 1 and 2.

Figure 4:
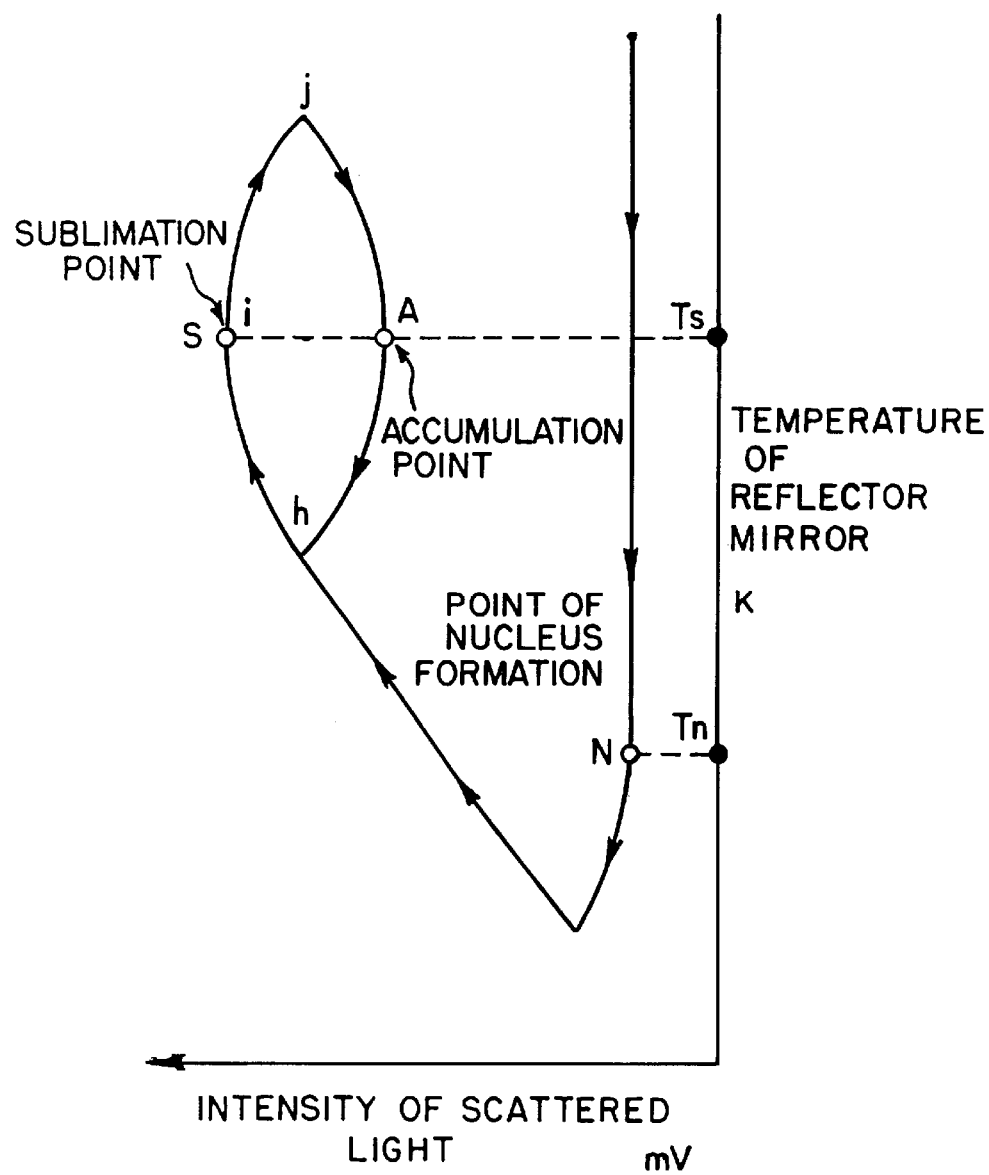
FIG. 4 is a graph showing, in association with FIG. 2, the relationship between the intensity of scattered light and each of the point of nucleus formation, the point of sublimation and the point of solidification of superposed layers.

FIG. 4 is a graph showing the relationship between the temperature of the reflector mirror and the intensity of scattered light with respect to a similar method of measurement. Since the reflected light is the same as the scattered light except that the variation in intensity is reversed, the following description concerns only the scattered light and no description is made about the reflected light.

When the cycles of heating and cooling the reflector mirror are repeated, the intensity of scattered light changes drawing a parabolic curve to form a loop as shown in FIG. 4.

Figure 5:
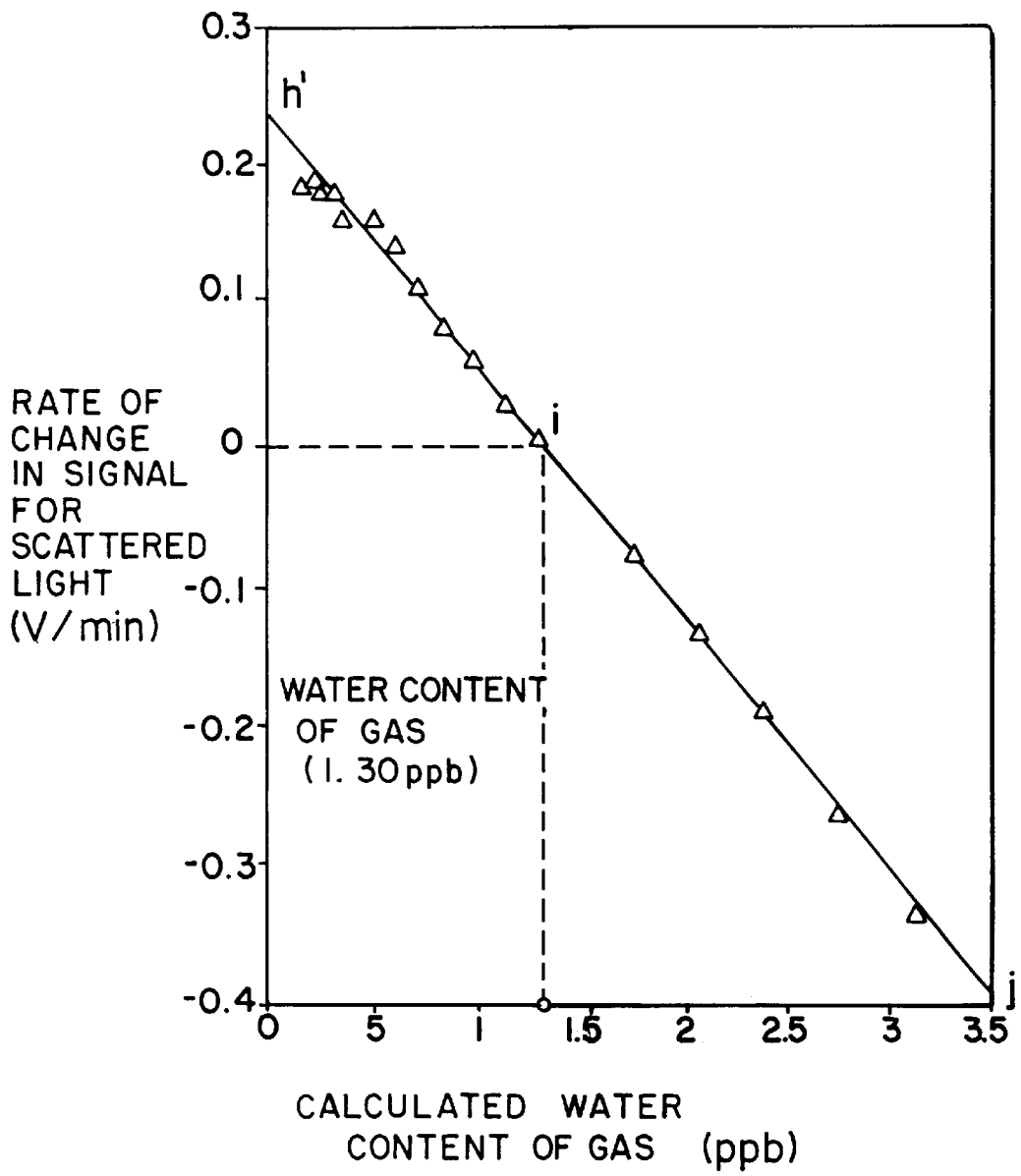
FIG. 5 is a graph by which the curve shown in FIG. 2 or 4 is differentiated to construct a straight line for determining a maximal point according to the invention.

FIG. 5 is a graph showing the relationship between the water content of a particular gas and the relative change in a signal for scattered light. Referring back to FIG. 4 the intensity of scattered light changes at points h, i and j drawing a curve when the temperature of the reflector mirror is varied. Assuming that the curve connecting points h, i and j represented a quadratic function, one may differentiate it and plot the result on a straight line, as shown in FIG. 5. In FIG. 5, points h', i' and j' correspond respectively to points h, i and j in FIG. 4. The water content of the gas as plotted on the horizontal axis represents the value as determined from the equation for the vapor pressure of ice.

One may safely conclude that the gas under consideration had a water content of 1.30 ppb. The conditions of the experiment were as follows:

$T_o = -90°$ C.

$R(T_s) = $ ca. 4° C./min n=ca. 0.67

$\Delta T =$ ca. 0.4° C.

Sample measured once for every two seconds.

Another characterizing part of the present invention is that it makes a special provision for the error resulting from noise that will unavoidably occur in measurements of the type contemplated by the present invention. If the peak intensity of scattered light is taken as the point of dew or frost condensation, noise makes it very difficult to read the correct point. However, if the point of dew or frost condensation is to be derived from the crest of a peak or the bottom of a valley as in the present invention, one may plot the actual points on the straight line obtained by differentiating a quadratic curve and determine the point of dew or frost condensation at the crest of a peak on the straight line obtained by the method of least squares. This insures the operator to obtain very precise and stable values even in the presence of noise.

Figure 6:
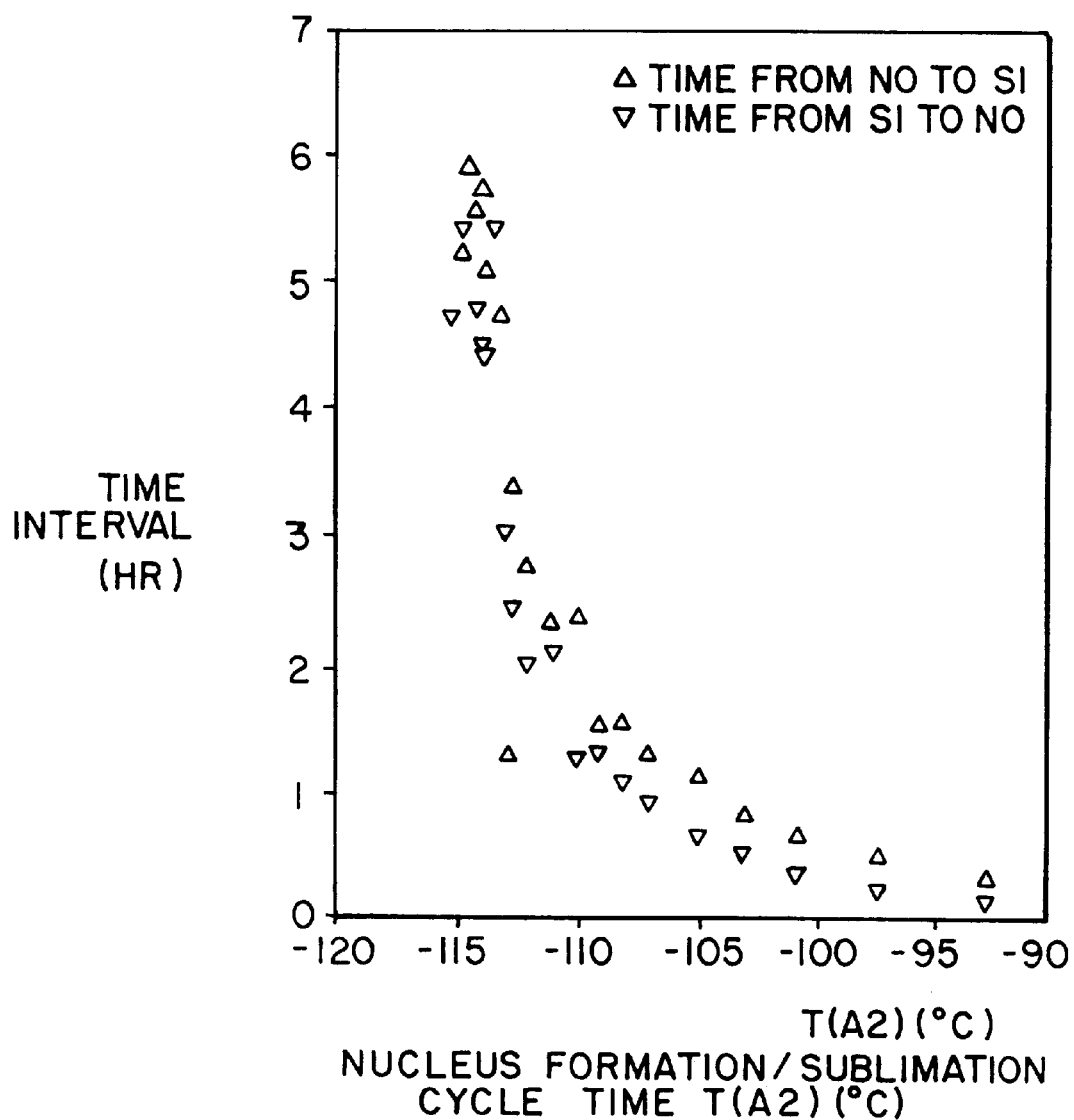
FIG. 6 is a graph showing the relationship between the nucleus formation-sublimation cycle time and the time interval for varying low dew points according to the prior art.

FIG. 6 shows a formation point (NO) of dew condensation or frost condensation in a conventional method to a point (S) where the strength of scattered light or reflected light becomes the largest and a point where dew condensation or frost condensation disappears from the point (S). It takes much time according to the conventional method.

Figure 7:
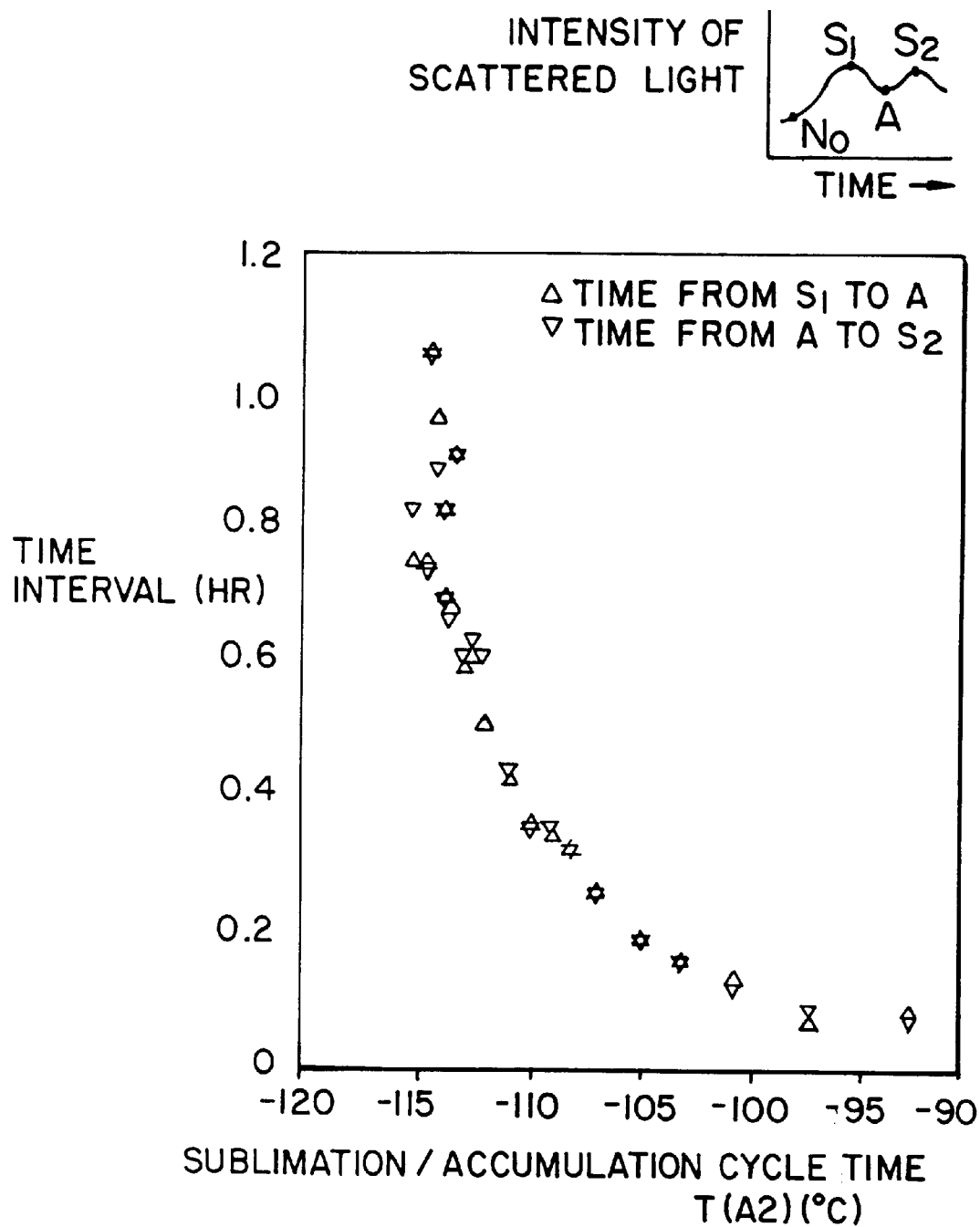
FIG. 7 is a graph showing the relationship between the nucleus formation-superposed layer solidification cycle time and the time interval for varying low dew points according to the invention.

FIG. 7A shows the relationship between sublimation points ($S_1$, $S_2$) and a lamination solidification point (A) of the present invention. It is apparent that the time is remarkably shortened according to the present invention.

Application

Some examples of measurement are shown below, using a low-temperature optical dew point meter.

Clean-up Phenomenon of a Tube

Figure 8:
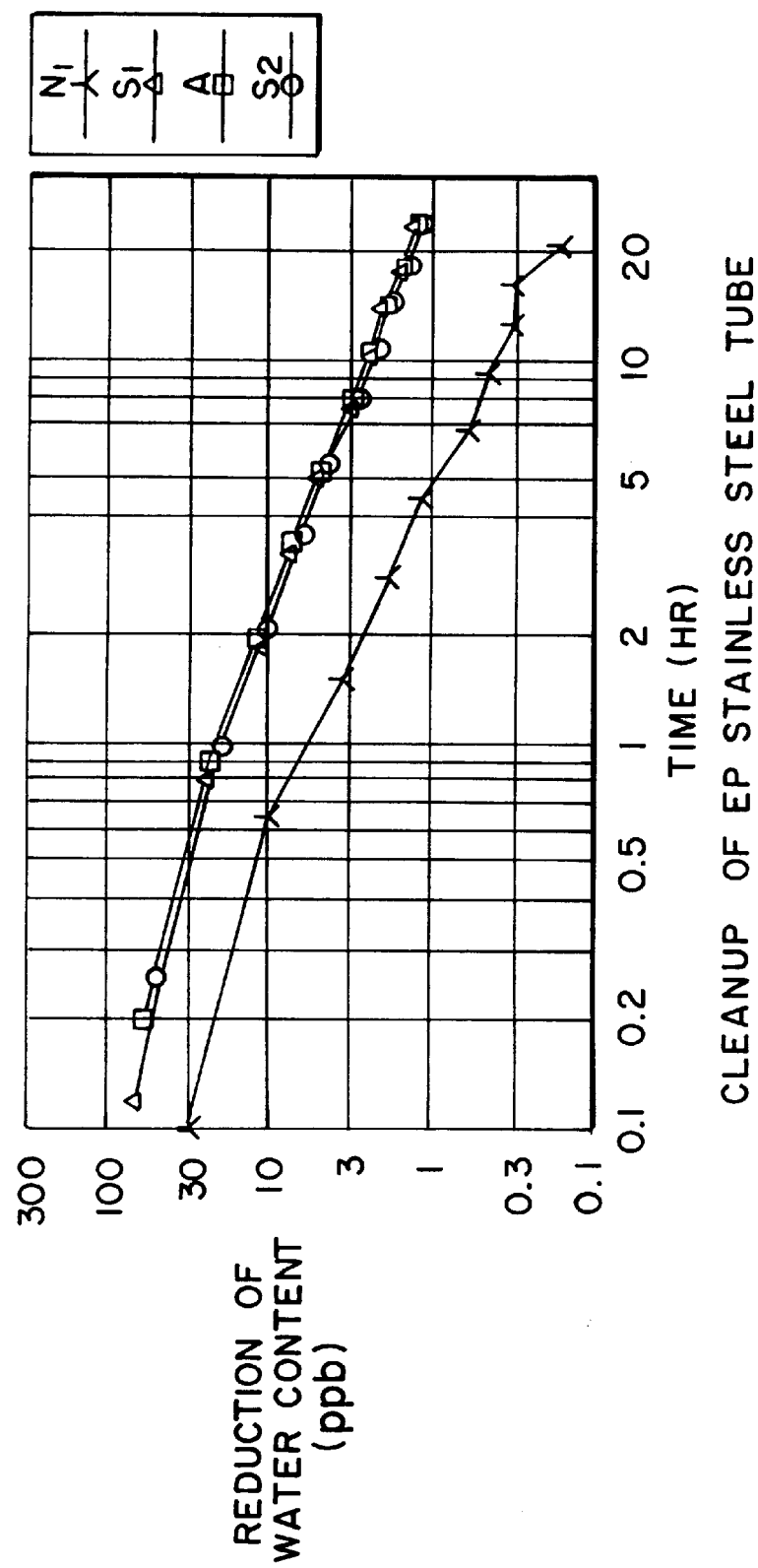
FIG. 8 is a graph showing the result of cleanup of a tube.

A clean-up phenomenon of a tube was measured when a $N_2$ gas purified by a getter purifier was passed through an EP tube of ¼ inch left to stand in an atmosphere. The temperatures of three points (S2, N3, S4) for the measurement of a dew condensation point (N1) and an equilibrium point measured with time are shown in FIG. 8. In this, equilibrium points are calculated in terms of moisture temperatures, and dew condensation points are plotted values converted according to a vapor pressure curve of ice for convenience' sake. According to them, equilibrium points reduce almost linearly and catch a desorption phenomenon of moisture adsorbed to the surface of the tube well. To the contrary, dew condensation points show low values in comparison with those of equilibrium points.

Effects of $O_2$ Passivation Treatment

Figure 9:
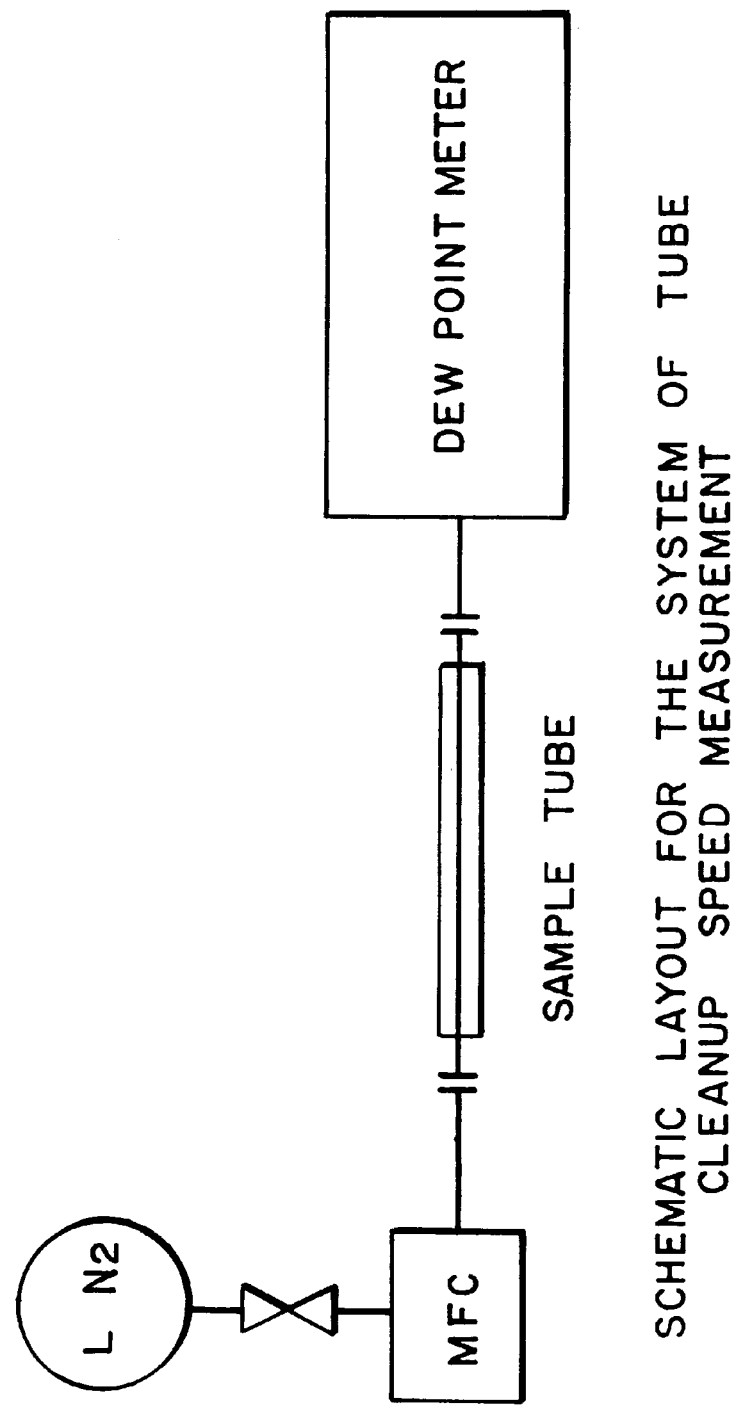
FIG. 9 shows a system for measuring the tube cleanup rate.

The above $O_2$ passivation-treated tube was compared with a non-treated tube. In FIG. 9 is shown a system practiced. In measurement, $N_2$ gas with a ultra-low dew point in which $LN_2$ was evaporated was used. The amount of the gas was controlled by MFC and passed through a tube to be measured and a clean-up speed was measured. As tubes to be measured, those with outer diameters of ⅜ inches and 1 inch were used.

Figure 10:
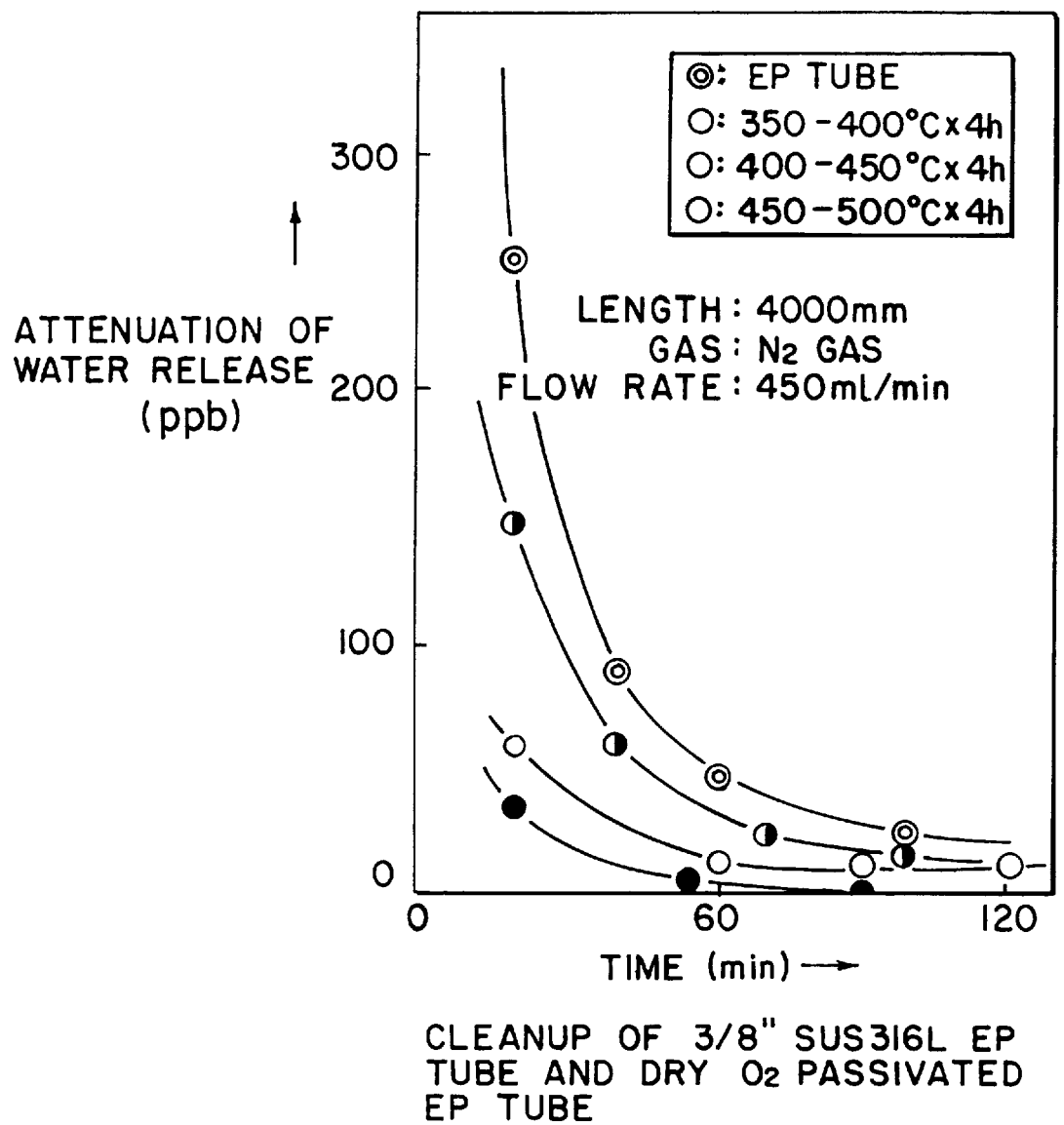
FIG. 10 is a graph showing the results of a cleanup experiment.
Figure 11:
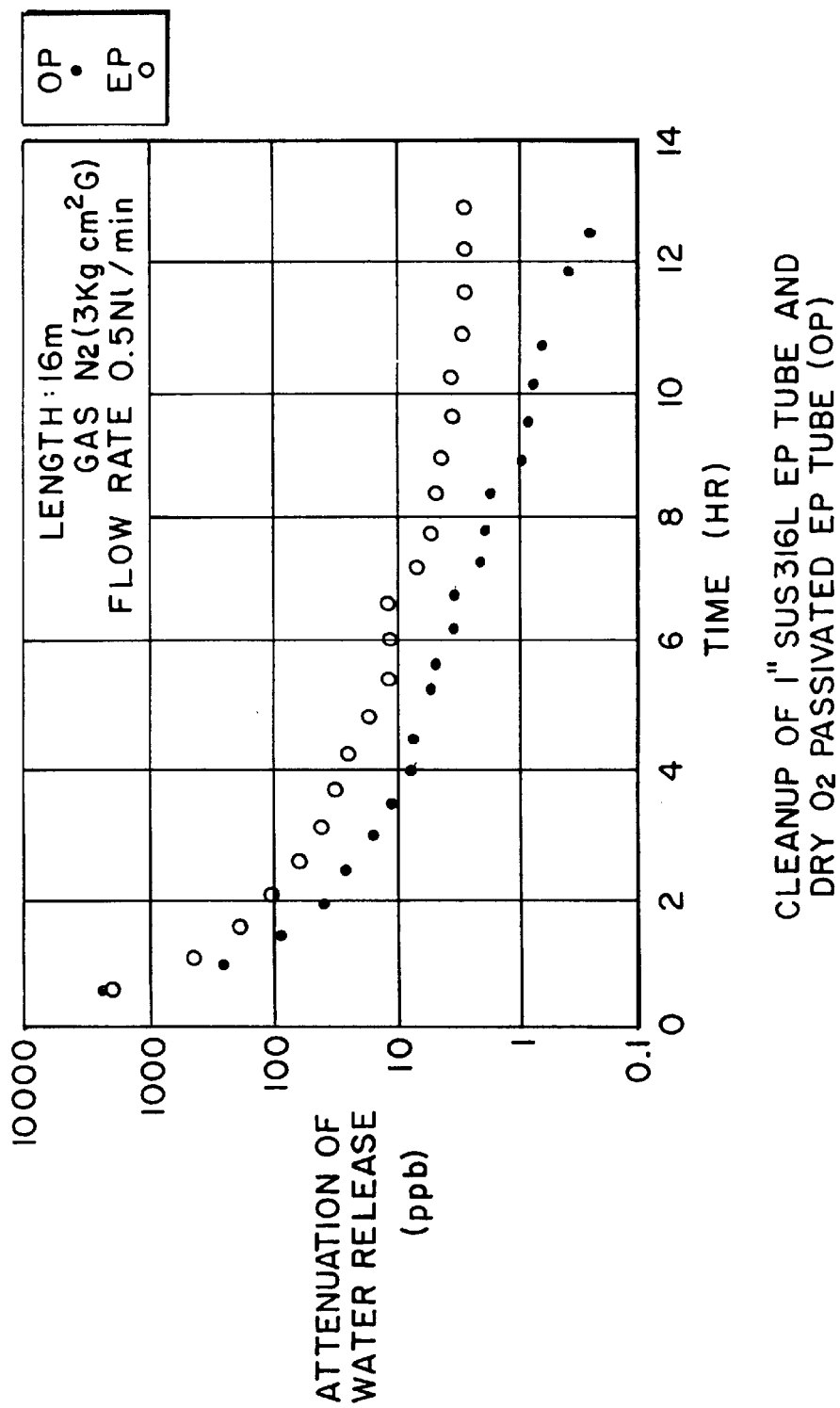
FIG. 11 is a graph showing the results of another cleanup experiment.

Another group of tubes having an outside diameter of ⅜ inch were passivated with $O_2$ at different temperatures. The results are shown in FIG. 10. Obviously, the clean-up speed was the slowest with the untreated electropolished EP tube and the fastest at temperatures of 400 and 450° C. FIG. 10 also shows that the behavior of water release from the inner surface tube was dependent on the passivation temperature and that an optimal passivation temperature can be determined from the behavior of water release. FIG. 11 compares the results of clean-up between a 1" SUS 316 LEP tube and a 16-mm long tube that was $O_2$ passivated.

Dew Point and Moisture Condensation

It is a well-known fact that a dew point and a moisture condensation can be converted into each other. As an actual method of showing a moisture content, units such as [° C.] and [ppm] are used together. Hereinafter, the conversion will be described. A moisture meter measured a moisture content according to its properties and converts it into a dew point. On the other hand, a dew point meter measured a dew point and converts it into a moisture content. These conversions are carried out by means of saturated vapor pressure according to the ratio of partial pressure and total pressure. since saturated vapor pressure is a function of a temperature, the relationship between a dew point and a moisture concentration can be obtained easily by finding the ratio of partial pressure and total pressure at a certain temperature. Therefore, generally, since a dew point is a phase change point in atmospheric pressure, namely, a dew condensation (frost condensation) point, total pressure takes atmospheric pressure. In case of employing this method, however, there are some points to be cared about, which will be described below:

1) There are many reports about saturated vapor pressure curves of water and each of them is a little different from others.
2) Conversion is capable of being carried out only in such a case when the complete equilibrium, namely, the state of saturation is measured because of the use of saturated vapor pressure.

By taking these points into consideration, the conversion of a dew point and a moisture concentration becomes possible. Though a conversion chart of a dew point and a moisture concentration up to −100° C. is shown in JIS K0512 (hydrogen), there is no conversion chart below −100° C. defined. Accordingly, it will be converted by means of an extrapolation line of a saturated vapor pressure curve of water, as mentioned above. At present, the most reliable equation is as follows:

$$\log_{10} PH_2O = -2445.5646/T + 8.2312 \log_{10} T - 0.01677006T + 1.20514 \times 10^{-8}T^2 - 6.757169 \, C = PH_2O/760 \cdot 10^9$$

T: Absolute temperature [K] (dew point)
$PH_2O$: Saturated vapor pressure water [mmHg]
C: Moisture concentration [ppb]

The above equation is reproduced from International Critical Tables of Numerical Data, Physics, Chemistry and Technology, Volume III, p. 210, National Research Council of USA (1928).

Figure 12:
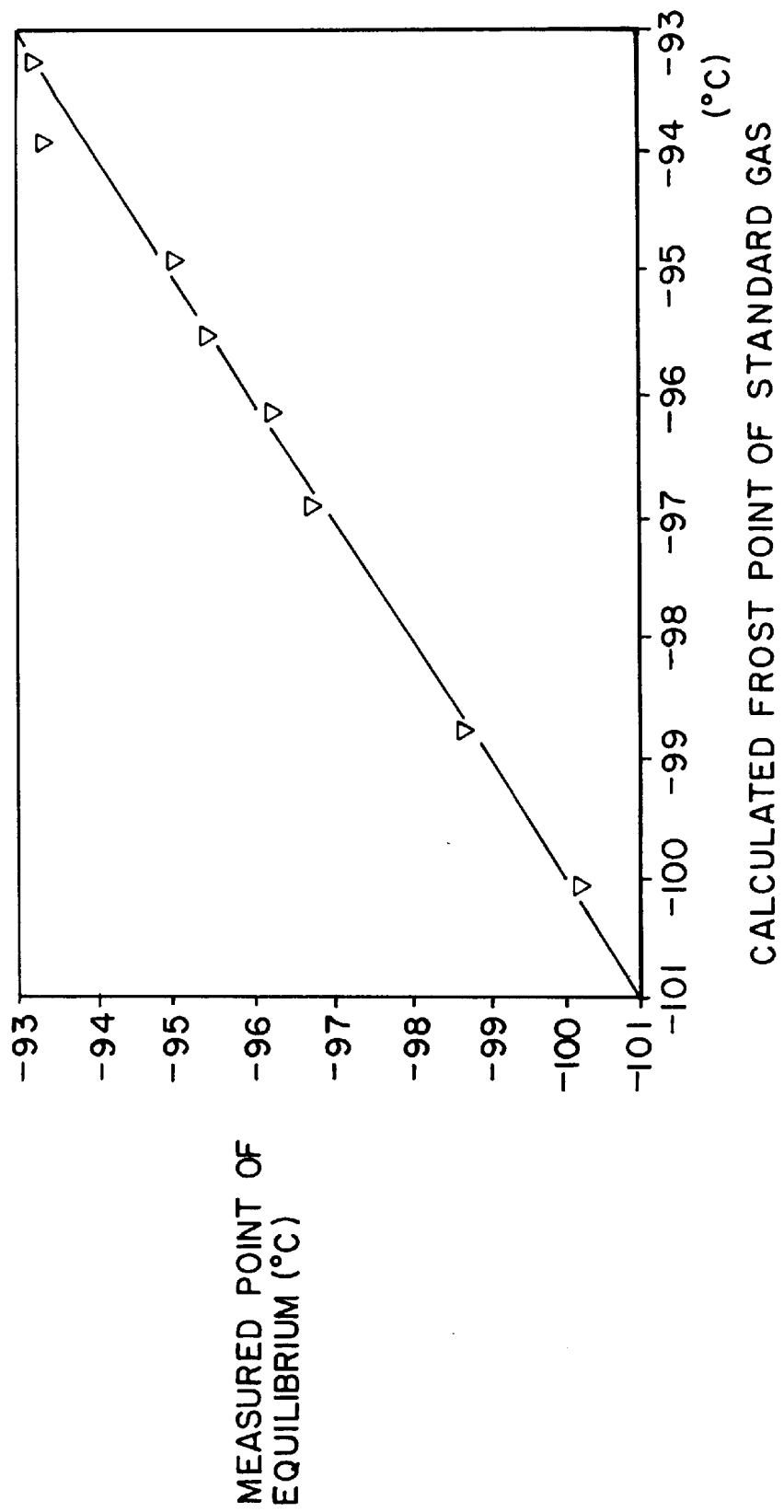
FIG. 12 is a graph showing the relationship between the frost point of a standard gas and the measured equilibria.
Figure 13:
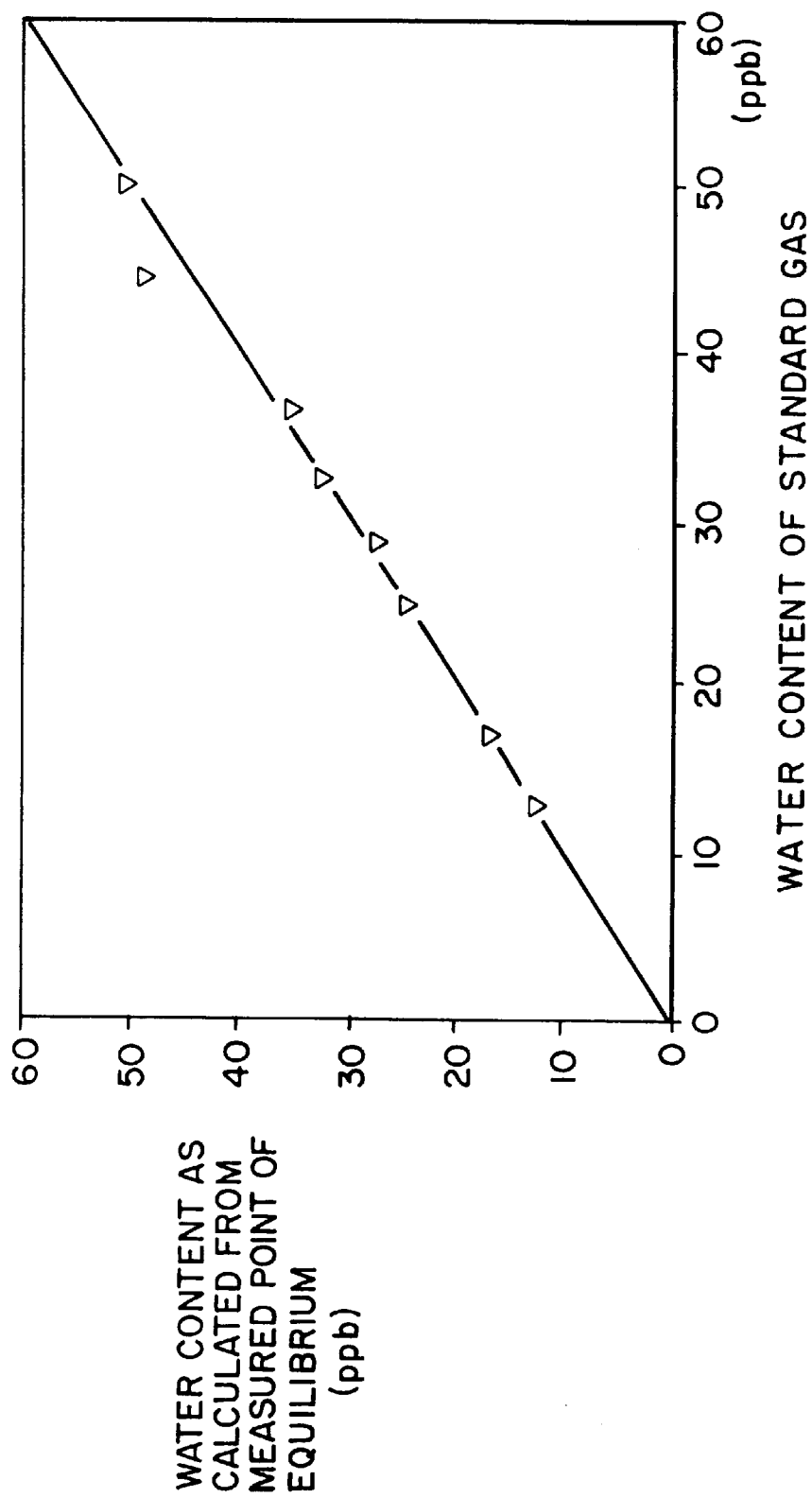
FIG. 13 is a graph showing the relationship between the water content of a standard gas and the data measured at the equilibria.

FIG. 12 shows the relationship between the dew point of a standard gas (whose moisture content is known) and the equilibrium point (C) measured according to the present invention. FIG. 13 shows the relationship between the moisture of a standard gas and the actual EP (equilibrium point) measured moisture. From FIGS. 12 and 13, it is apparent that the method of the present invention can measure the moisture in the gas very correctly.

The present invention is described below from a mechanistic viewpoint with reference to accompanying drawings. The dew point meter shown in those drawings is merely intended for illustrative purposes and will in no way limit the scope of the present invention.

Figure 14:
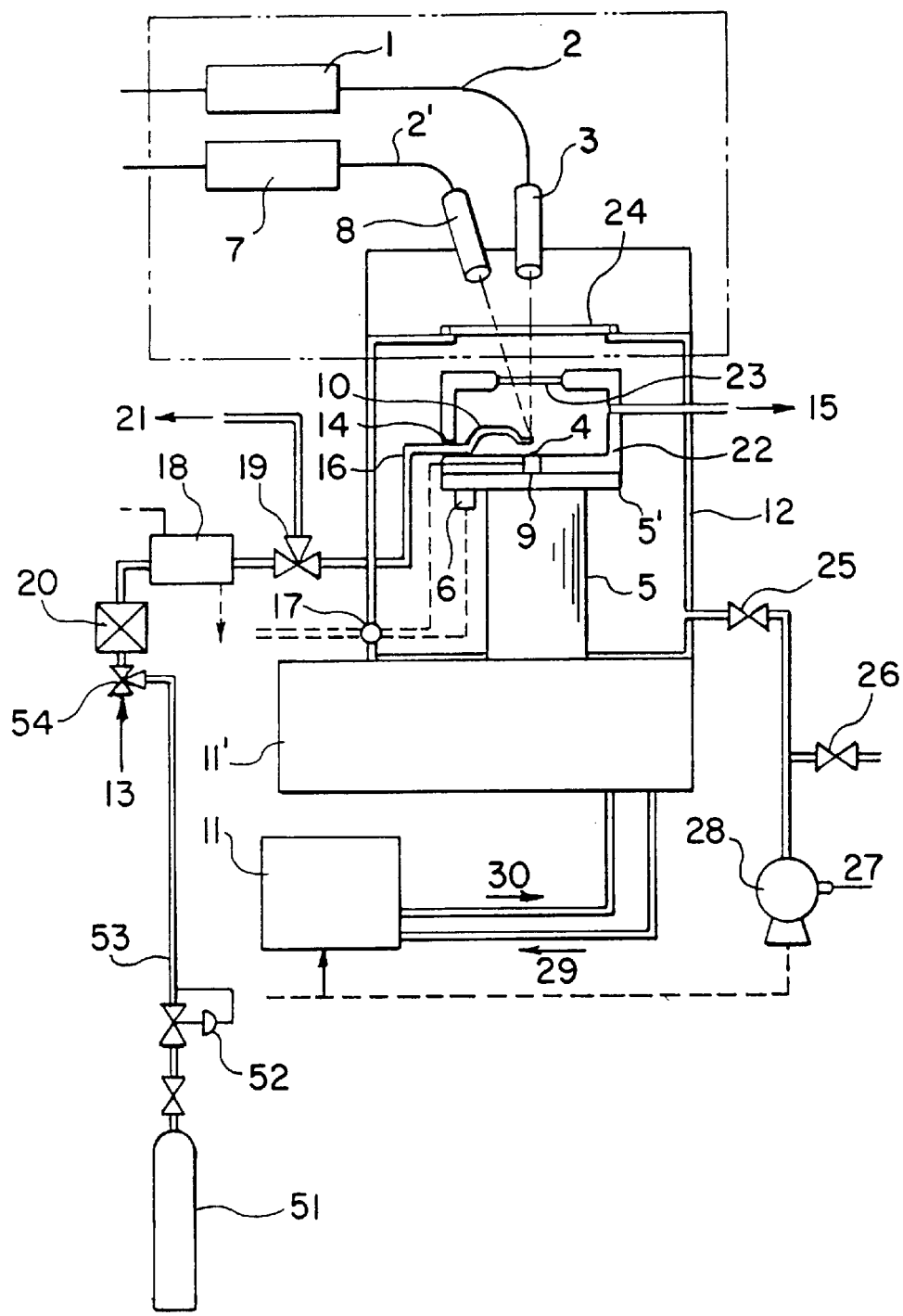
FIG. 14 shows a preferred apparatus for implementing the invention.

FIG. 14 shows a first example of the invention. The cooling system uses a helium refrigerator. Helium gas as compressed with a circulating helium compressor 11 circulates within a loop containing a line 30, a drive mechanism 11', a freeze generating portion 5, the drive mechanism 11' and a line 29. The freeze generating portion 5 has a piston or depressor fitted into a stainless steel cylinder and it is driven up and down by means of the drive mechanism 11' to generate freeze on the chill surface 5' at the top of the cylinder. A metallic cell (hereunder referred to simply as "cell") is provided in such a way as to make intimate thermal contact with the chill surface 5'. The cell 22 is partly made of a light-transmissive material 23 such as glass. Placed on the bottom of the cell 22 is a reflector mirror 4 that is composed of a smooth-surfaced silicon wafer and that makes intimate thermal contact with the inner surface of the cell 22. A temperature sensor 9 such as a thermocouple or a resistance thermometer is inserted into the bottom of the cell 22.

A sample gas to be measured for its dew point is introduced into the system through a gas inlet 13, passes through a filter 20, has its flow rate controlled by means of an automatic flow adjuster 18 such as a mass flow controller and a three-way vale 19 before it leaves the system via a gas outlet 21. The higher the purge rate, the shorter the time required for the sample gas line to reach equilibrium. The sample gas then flows into the cell 22 via 16 and the line penetrating the cell consists of a thin-walled stainless steel tube. Within the cell 22, the gas is subsequently blown against the reflector mirror 4 placed on the bottom and thereafter leaves the system via a gas outlet 15. To ensure quick response, the gas line extending from the inlet 13 through the system to 10 is preferably made of a stainless steel tube of ¼", ⅛" or ¹⁄₁₆" in diameter that is highly smoothened on the inner surface by electropolishing or some other suitable method and that experiences less moisture adsorption and desorption or water release from the inside.

The light issuing from LED 11 travels through an optical fiber 2 so that it is condensed to a certain extend and further condensed by lens 3. Thereafter, the light passes through windows 24 and 23 each made of a light-transparent material and it falls on reflector mirror 4 at a right angle to the surface. The light scattered from the surface of the reflector mirror is condensed by condenser lens 8 provided in a direction deviating from the angle of reflection of the light projected from lens 3 and the thus condensed light travels through an optical fiber 2' to be picked up by PN photodiode 7. The dew formation on the surface of the reflector mirror can be determined by the above-described procedure from the relationship between the change in the intensity of scattered light and the temperature.

Cold portions such as cell 22, freeze generating portion 5 of the helium refrigerator and chill surface 5' have to be insulated thermally from the surrounding atmosphere. To meet this requirement, those portions are isolated from the surrounding atmosphere by means of an airtight chamber 12 containing electric wiring connectors 17 and insulated thermally by evacuation with a line comprising vacuum valves 25 and 26 and a vacuum pump 28. When the equilibrium points, i.e., the point of sublimation and the point of solidification of superposed layers, are measured continuously with the system shown in FIG. 14, the sensitivity of measurement will drop on account of contamination of the mirror surface. This phenomenon can be identified by a change in the slope of the straight line shown in FIG. 5. The contamination of the mirror surface could occasionally be reduced by elevating the temperature of the mirror surface by at least 40–50° C. A more effective way is to perform automatic cleaning of the cell with $CO_2$. Shown by 51 in FIG. 14 is a cylinder containing liquified $CO_2$ that has been specifically purified to 99.999% and above; 52 is a pressure regulating valve, 53 is a pipe, and 54 is a valve. The $CO_2$ supply mechanism may be connected to the line for introducing the gas to be measured or, alternatively, it may be designed as a mechanism that permits $CO_2$ to be blown against the reflector mirror independently of the gas to be measured.

Figure 15:
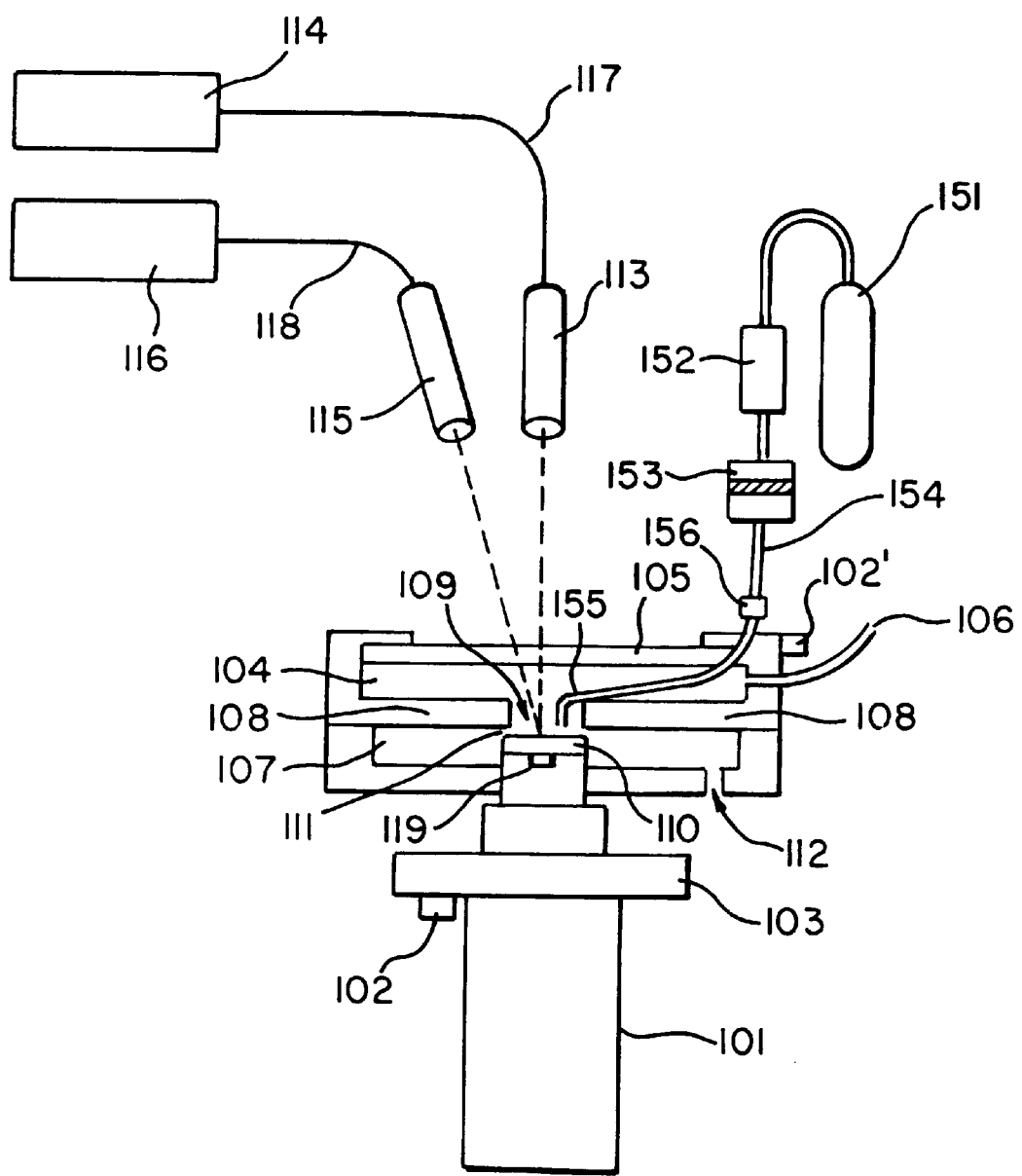
FIG. 15 shows another preferred apparatus for implementing the invention.

FIG. 15 shows another embodiment of the invention. Shown by 101 is a freeze generating portion; 102 is a heater; 103 is a chill surface; 104 is compartment A which is made of a good heat conductor such as gold, silver, copper, aluminum, silicon, nickel or chromium; 105 is a window made of a light-transmissive material such as glass; 106 is an inlet for the gas to be measured; 107 is compartment B which is separated from compartment A 104 by a partition 108 having a hole 109 in it. Reflector mirror 110 is provided below the hole 109. Shown by 111 is a gap between the reflector mirror 110 and the partition 108. The gap 111 is preferably small but if it is designed to be unduly small, the slightest manufacturing error may cause contact between the reflector mirror 110 and the partition 108. To avoid this problem, the gap 111 is preferably of a size between 0.1 and 2.0 mm. At least part of compartment B 107 is made of a poor heat conductor such as stainless steel, Cu—Ni alloy, glass, ceramics or plastics (e.g. fluoro, polyimide and silicone resins) and this is in order to insure that compartment A will not be cooled by the chill surface 103. shown by 112 is a gas outlet; 114 is a light source; and 113 is a condenser lens. The light source 114 is typically an LED emitting at a specified wavelength. Shown by 115 is another condenser lens; 116 is a photodetector; and 117 and 118 are optical fibers.

The water content of a certain gas can be measured with the system of FIG. 15 by the following procedure. First, the gas of interest is supplied through inlet 106 into compartment A 104 which is controlled at a specified temperature by means of heater 102'. The gas passes through the hole 109 to contact reflector mirror 110, forming dew or frost on its surface. The gas then passes through gap 111 to enter compartment B 107, from which it emerges through outlet 112. The size of gap 111 is small enough to ensure that the gas flowing from compartment A 104 to compartment B 107 via hole 109 does not fail to contact the reflector mirror. The light emerging from the source 114 is condensed by lens 113 such that it is focused at the dew or frost formed on the surface of reflector mirror 110 and the dew point or frost point is determined by the procedure already described above.

shown by 151 is a liquefied $CO_2$ cylinder; 152 is an adsorber tower for removing water and oil; 153 is a dust filter; 154 is a pipe; 155 is a nozzle; and 156 is a pressure regulating valve. The $CO_2$ supply mechanism may be connected to line 106 for introducing the gas to be measured.

The freeze generating portion is typically provided by a helium refrigerator (not shown) but it may be operated using other refrigerants such as liquefied nitrogen.

It is generally preferred that the space within compartment A 104 of the system shown in FIG. 15 has a volume of 0.5–5 cm$^3$. The compartment A may have any desired planar shape.

In FIG. 15, compartment A is located above compartment B but this is not the sole case of the invention and compartment B may be located above compartment A. Alternatively, the two compartments may be placed side by side on a horizontal plane.

Figure 16:
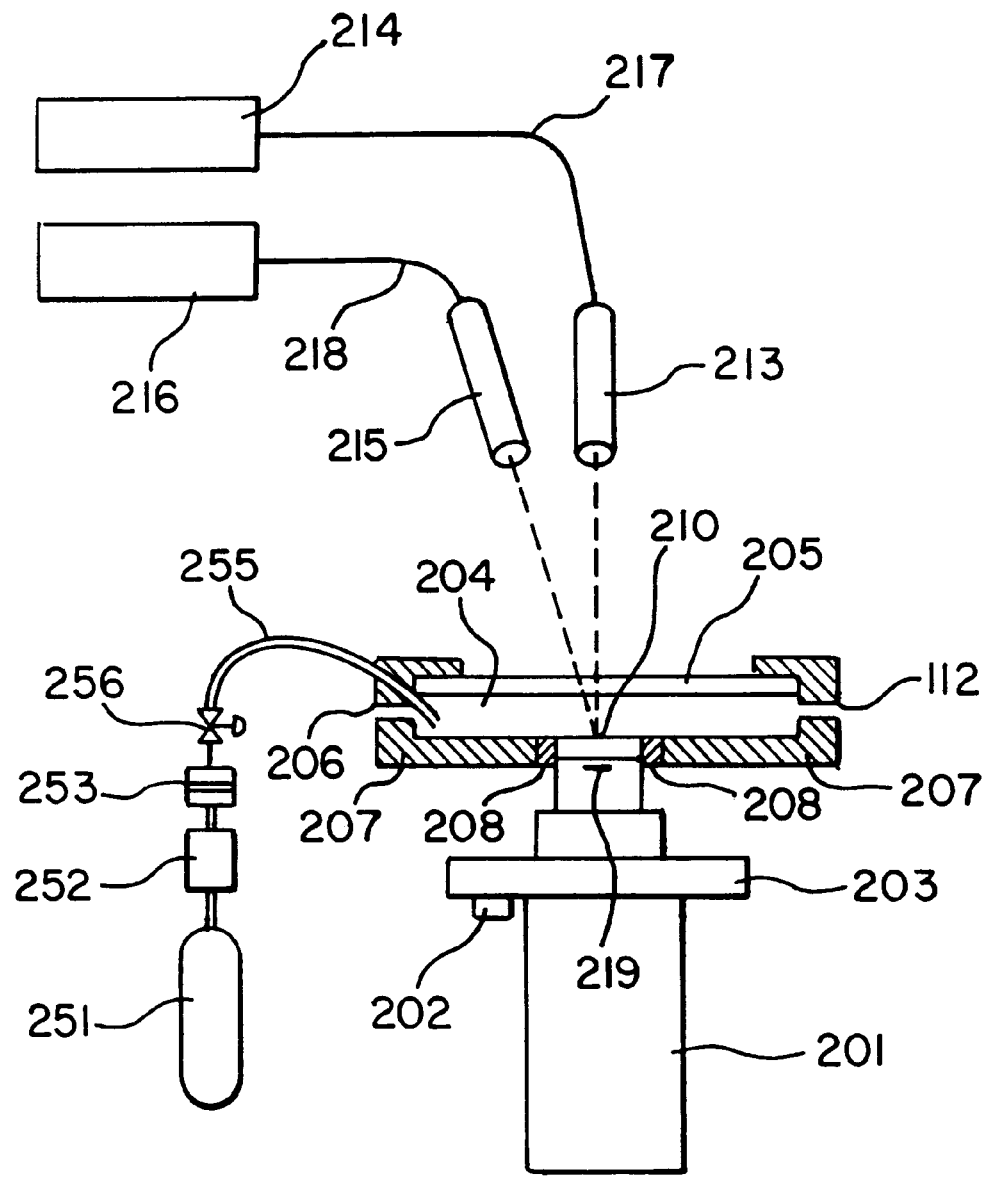
FIG. 16 shows yet another preferred apparatus for implementing the invention.

Still another embodiment of the invention is shown in FIG. 16. Shown by 201 is a freeze generating portion; 202 is a heater; 203 is a chill surface; 204 is a measuring compartment that consists of two portions 207 and 208, 207 being made of a good heat conductor such as gold, silver, copper, aluminum, silicon, nickel or chromium and 208 being made of a poor heat conductor such as stainless steel, Cu—Ni alloy, glass, ceramics, or plastics (fluoro, polyimide and silicon resins). Shown by 205 is a window made of a light-transmissive material such as glass; 206 is an inlet for the gas to be measured; 210 is a reflector mirror; 212 is a gas outlet; 213 is a light condensing lens; 214 is a light source such as LED; 215 is also a condenser lens; 216 is a photodetector; and 217 and 218 are optical fibers.

To measure the water content of the gas of interest using the system shown in FIG. 16, the gas is first introduced into compartment 204 via inlet 206 without being cooled; the gas contacts the reflector mirror 210 to form dew or frost on its surface. The gas thereafter leaves compartment 204 via outlet 212. The light emerging from the source 214 is condensed by lens 213 such that it is focused at the dew or frost formed on the reflector mirror and the dew or frost point can be determined by the method already described above.

Figure 17:
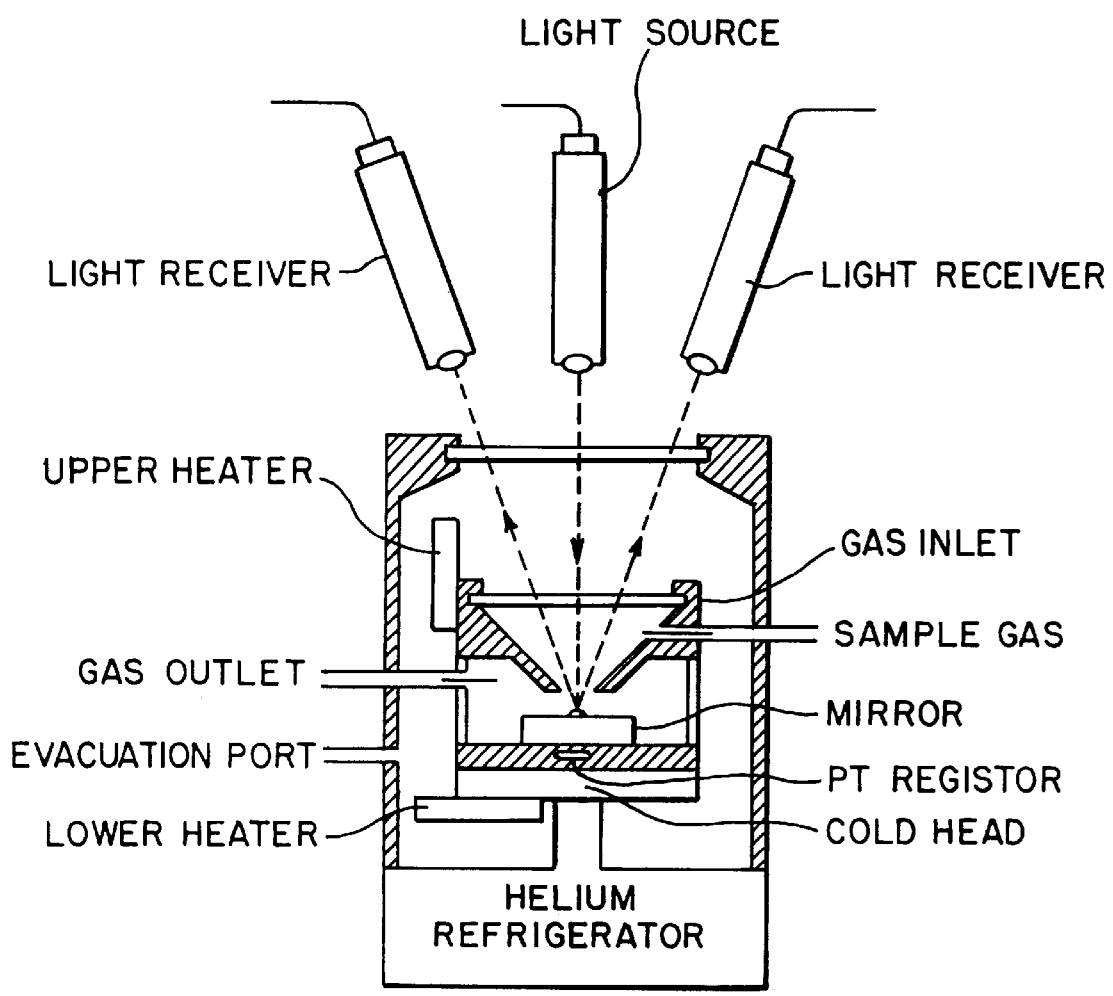
FIG. 17 shows another preferred apparatus for implementing the invention.
Figure 18:
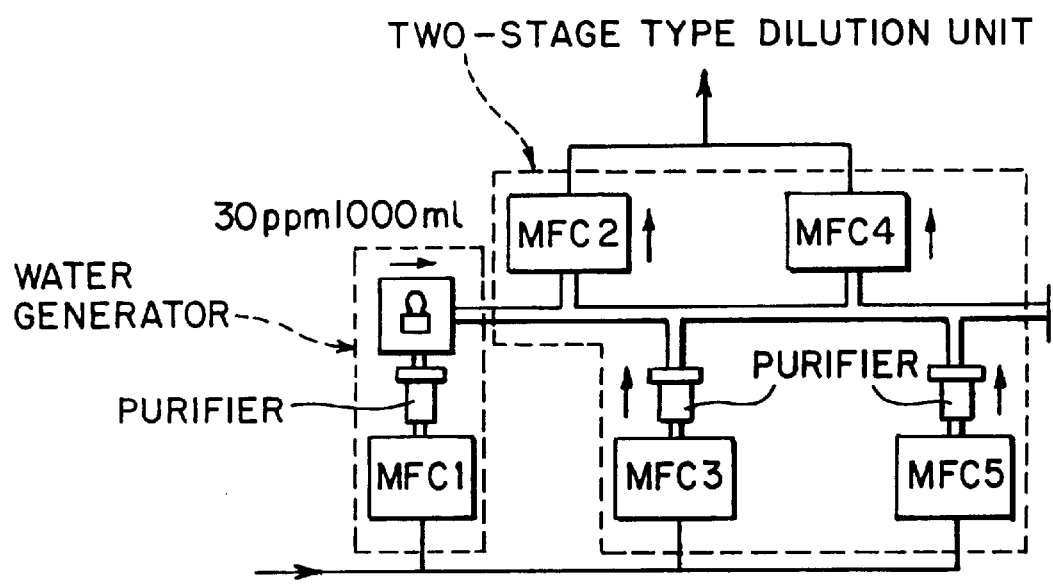
FIG. 18 is a flow sheet of the apparatus for generating a standard water content that was used to provide the data shown in FIGS. 12 and 13.

A system according to yet another embodiment of the invention is shown in FIG. 17. The system differs from that of FIG. 15 in that hole 109 is funnel-shaped and that the scattered light is picked up by the photodetector after it is condensed by two or more lenses positioned in different directions so as to provide a higher sensitivity. A standard gas capable of generating a desired water content that was used in experiments for water content measurement by the measurement of equilibrium points was produced by diluting a 10-ppm standard gas with an apparatus of the type shown in FIG. 18. The apparatus consists of the combination of mass flow controllers (MFC) commercially available from Hitachi Tokyo Electronics Co., Ltd.

Figure 19:
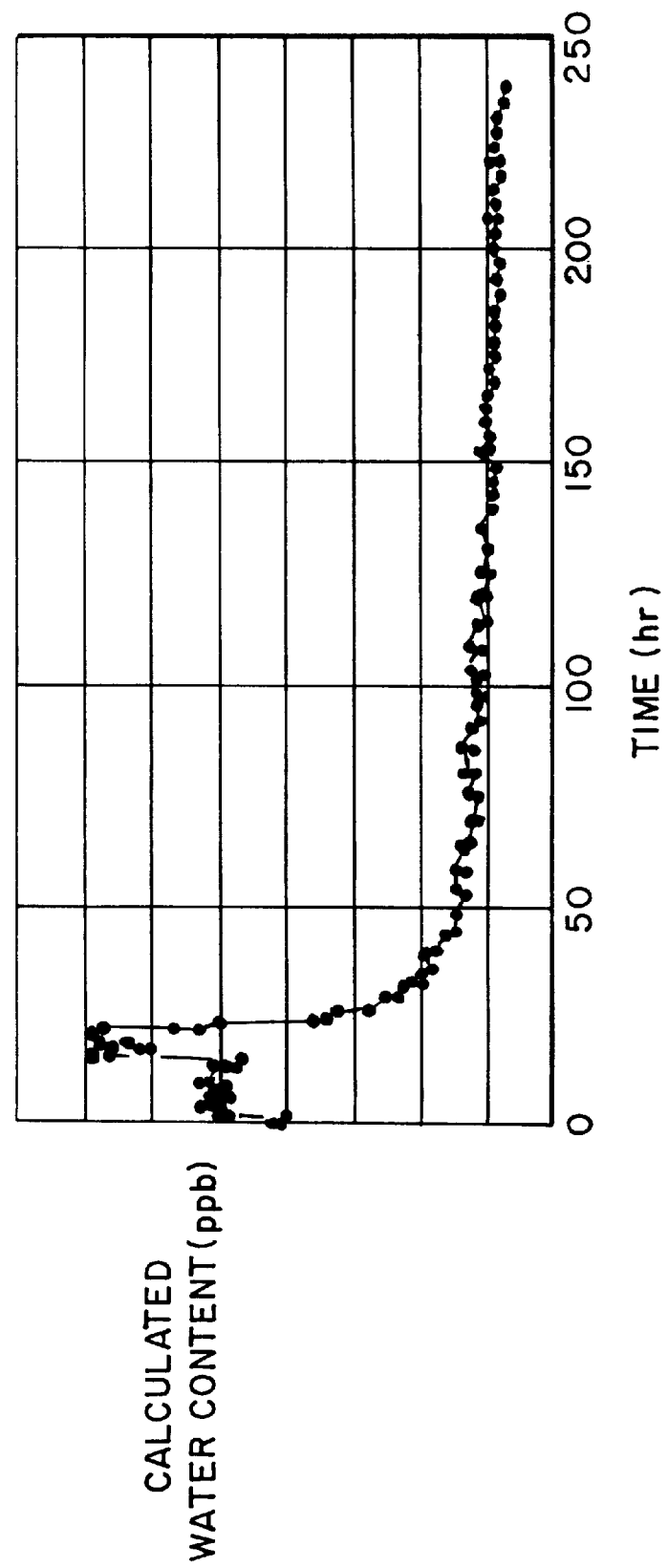
FIG. 19 is a graph showing the values obtained by a continuous measurement of the water concentration profile of a standard gas.

FIG. 19 is a graph showing the results of an experiment conducted to measure the water content of a gas that was admitted into a dew point meter after it was passed through a getter purifier of SAES GETTER Inc. which used a zirconium alloy capable of removing impurities at an elevated temperature of 400° C. In the initial period of the experiment, the gas was not passed through the water remover. After passage through the getter purifier, the water content dropped to 1 ppb and levels near 1 ppb were maintained for 200 h or more. This results shows that if the dew or frost point is measured in accordance with the invention, stable values can be provided for a prolonged time.

EXAMPLE 1

Figure 20:
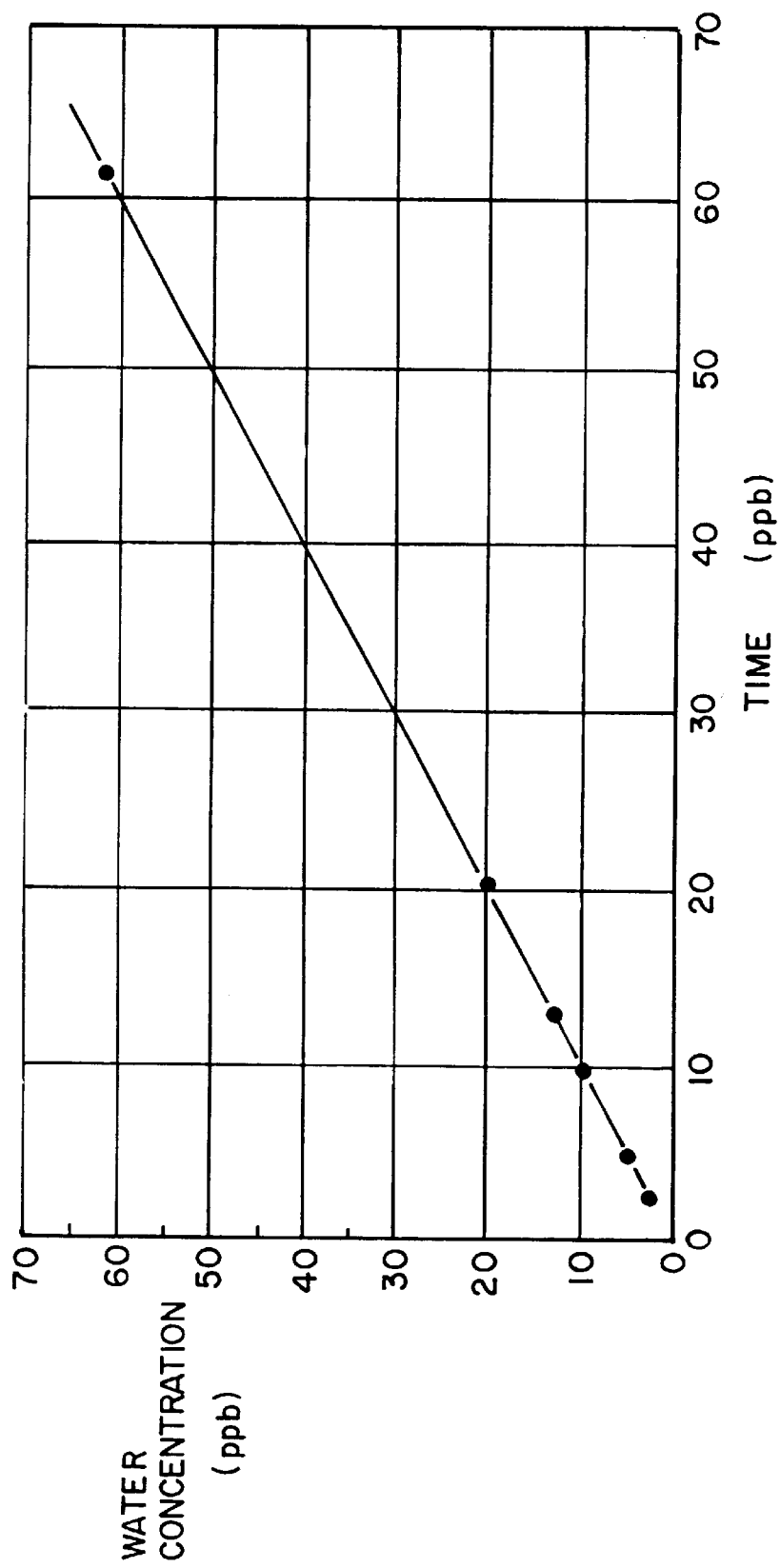
FIG. 20 is a graph showing the result of evaluation of a cryogenic optical dew point meter using the apparatus for generating a standard water content.

To evaluate the performance of a cryogenic optical dew point meter, $N_2$ gas from a generator capable of generating water at the ppb level was measured for its dew point and the result is shown in FIG. 20. The generator was MG-20 which is commercially available from Hitachi Tokyo Electronics Co., Ltd. which operated on the principle of dilution by a volumetric method of the water produced by the combination of a gravimetric and a diffusion method. The diluent gas was prepared by removing water from a gas through a getter purifier of SAES GETTER Inc. According to FIG. 20, the values measured with the cryogenic optical dew point meter were in good agreement with the data obtained by the water generator and the matching was assured to very small values at the ppb level. Hence, it is verified that the values measured by the dew point method are in good agreement with the data obtained by the gravimetric method.

EXAMPLE 2

Figure 21:
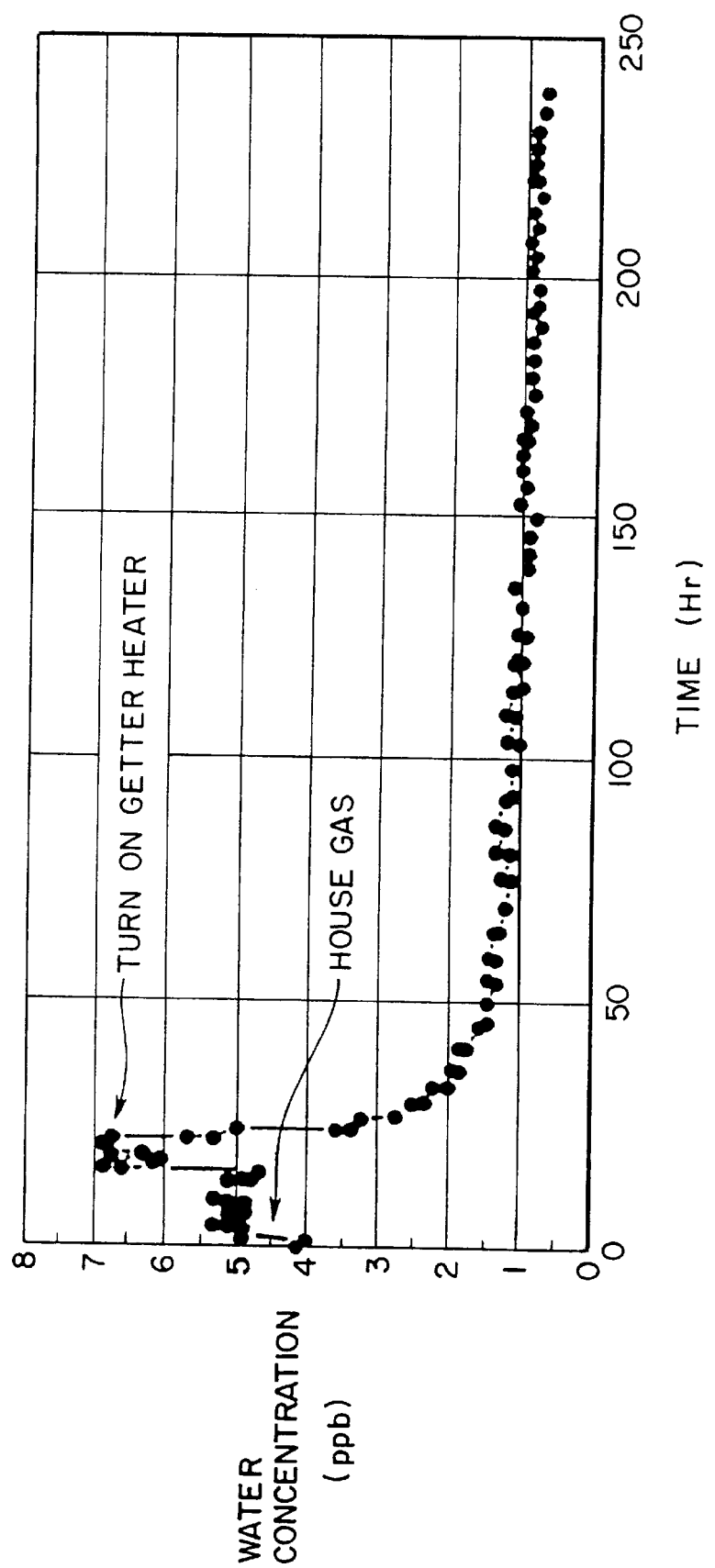
FIG. 21 is a graph showing the result of evaluation of a getter purifier.
Figure 22:
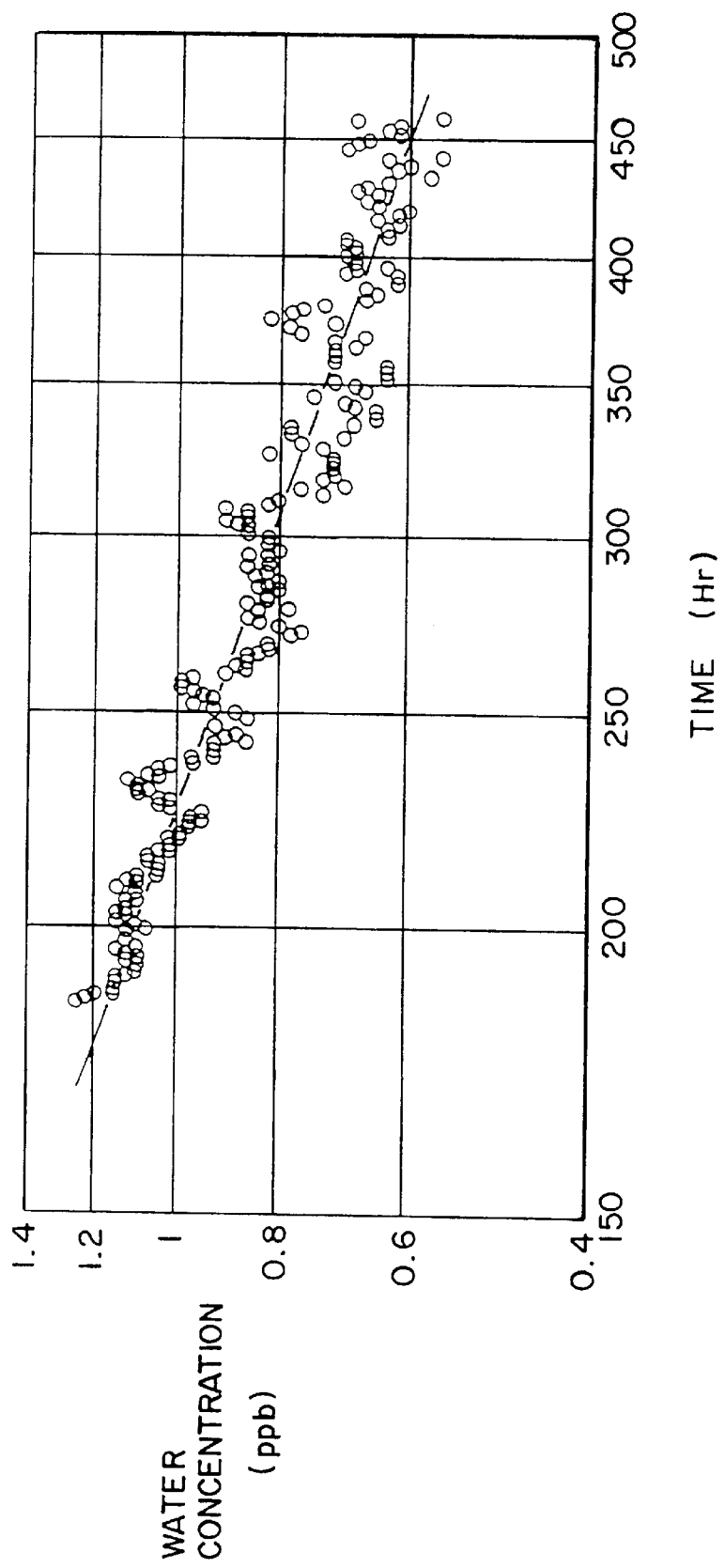
FIG. 22 is a graph showing the relationship between time and water concentration ($\leq 1$ ppb)
Figure 23:
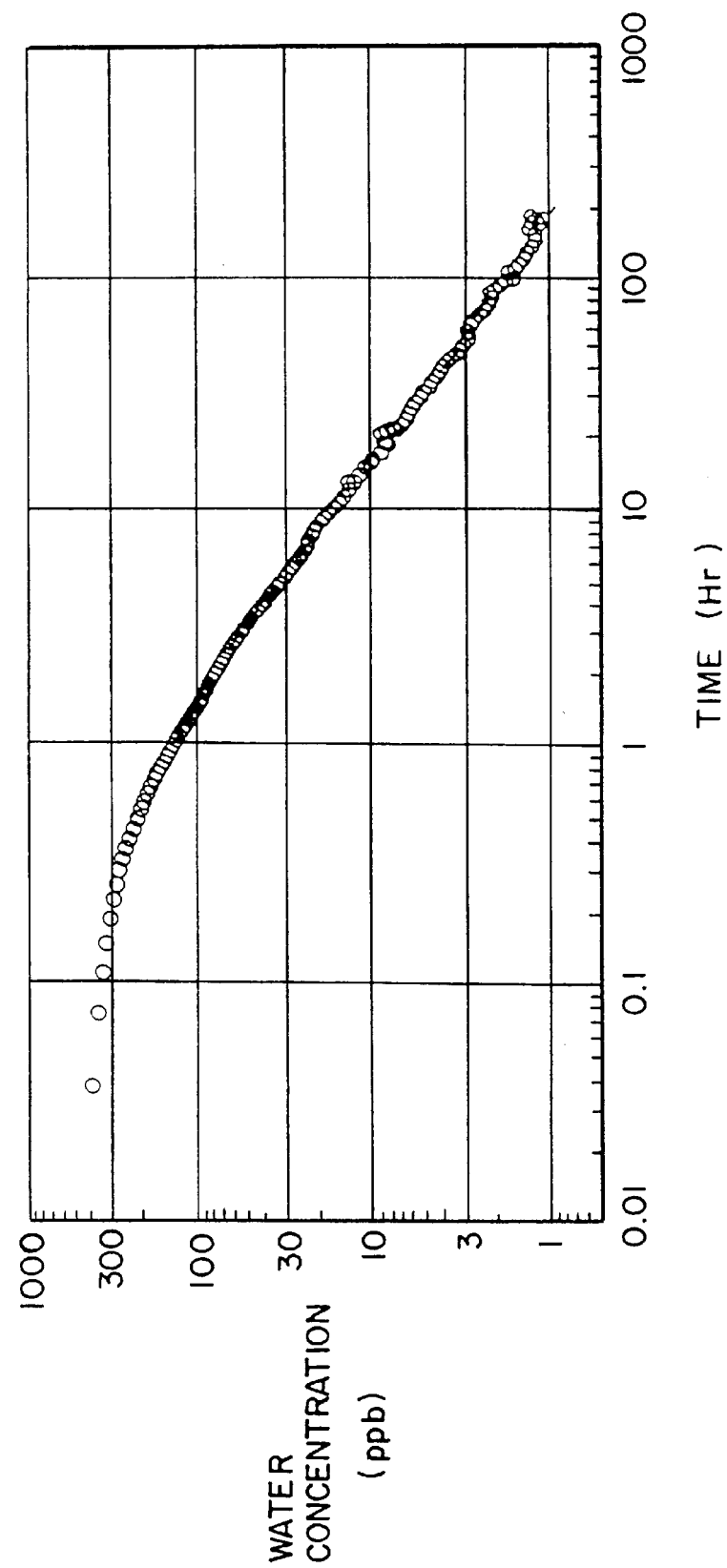
FIG. 23 is a graph showing the relationship between time and water concentration (>1 ppb).

The gas supply system was evaluated for its performance by measuring the gas at the exit of the getter purifier of SAES GETTER Inc. The result is shown in FIG. 21 as the data of monitoring the time-dependent change in the water concentration of the inlet gas (ca. 5 ppb) after passage through the getter purifier. Obviously, the wafer released from the wall surface was detected right after the heater in the getter purifier was turned on and as the temperature of the gettering material rose to provide an enhanced purifying effect, an increasing amount of water was removed. It is also clear from FIG. 21 that the cryogenic optical dew point meter was capable of consistent measurement until the water content decreased below 1 ppb. The cryogenic optical dew point meter was applied to a dry-down test on the piping and its performance was evaluated for the case where the water content was 1 ppb or less (FIG. 22) and for the case where the water content was more than 1 ppb (FIG. 23).

What is claimed is:

1. A method for determining the dew point of a gas containing a very small amount of water using an optical dew point meter including a reflector mirror, the temperature of which can be varied from room temperature to −80° C. or below, a means for contacting said reflector mirror with the gas to be measured, a means for irradiating said reflector mirror with focused rays of light and a detector for detecting changes in scattered light or reflected light from said reflector mirror due to the dew condensed on said reflector mirror, said method comprising the steps of:

contacting said reflector mirror with the gas to be measured;

applying said focused rays of light onto that part of the reflector mirror where it is contacted with said gas;

measuring the intensity of scattered light or reflected light from said reflector mirror;

gradually reducing the temperature of said reflector mirror, either before or while said reflector mirror and said gas contact, thereby condensing dew on said reflector mirror;

detecting a change in said measured intensity of said scattered light or reflected light, and measuring a maximum intensity value for said scattered light or a minimum value for said reflected light;

continuously reducing or elevating the temperature of said reflector mirror to obtain a constant intensity of said scattered light or reflected light; and determining the temperature of said reflector mirror at said constant light intensity, said determined reflector mirror temperature corresponding to the dew point.

2. A method according to claim 1 wherein after dew is formed on said reflector mirror, the temperature of said reflector mirror is gradually increased so that the dew at the dew point is not completely sublimed, and said maximum intensity of said scattered light is obtained or said minimum intensity of said reflected light is obtained, and then cooling the reflector mirror to obtain a minimum intensity value of scattered light or to obtain a maximum intensity value of said reflected light, and wherein the above operation is repeated at least one time.

3. A method according to claim 1 wherein the temperature of said reflector mirror is gradually reduced by cooling or elevated by heating said reflector mirror at a rate that is varied either stepwise or continuously generally along the curve represented by:

$$R(T)=R(T_0)[P'(T)/P'(T_0)]_n$$

where T: the temperature (K) of the reflector mirror;

$T_0$: any specific temperature (K) that can be selected from the range of from room temperature to the temperature of liquid nitrogen;

R(T): the cooling or heating rate (K/min) at a selected temperature (K) of the reflector mirror;

P'(T): the derived functions of the saturated vapor pressure of ice determined with the temperature (T) being taken as a variable;

$P'(T_0)$: a calculated value of the saturated vapor pressure of water at the specific temperature $T_0$; and n: the value so selected as to provide a substantially constant signal-to-noise ratio of at least 2 in the measurement of the change in said reflected light or said scattered light over a fixed temperature interval ΔT.

4. A method according to claim 3 wherein said cooling and heating rates are determined by applying the following equations for vapor pressure P'(T) and $P'(T_0)$:

$$\log_{10}PH_2O=-2445.5646/T+8.2312\log_{10}T-0.016770067T+1.20514\times10^{-5}T^2-6.757169$$

where T: the dew point on the absolute scale (K) and $PH_2O$: the saturated vapor pressure of water (mmHg).

5. The method of claim 1, wherein said light is laser light.

6. A method of determining the dew point of a gas containing a very small amount of water using an optical dew point meter including a reflector mirror the temperature of which can be varied from room temperature to −80° C. or below, a means for contacting said reflector mirror with the gas to be measured, a means for irradiating said reflector mirror with focused rays of light, and a detector for detecting changes in scattered light or reflected light due to the dew condensed on said reflector mirror, said method comprising the steps of:

contacting said reflector mirror with the gas to be measured;

applying said focused rays of light onto that part of the reflector mirror where it is contacted with said gas;

measuring the intensity of scattered light or reflected light from said reflector mirror;

gradually reducing the temperature of said reflector mirror, either before or while said reflector mirror and said gas contact, thereby condensing dew on said reflector mirror;

detecting a change in said measured intensity of said scattered light or reflected lights and measuring a maximum intensity value for said scattered light or a minimum value for said reflected light;

continuously reducing or elevating the temperature of said reflector mirror to obtain a constant intensity of said scattered light or reflected light; and determining the temperature of said mirror at said constant light intensity, said determined reflector mirror temperature corresponding to the dew point, wherein said maximum intensity of said scattered light or said minimum intensity of said reflected light is determined by differentiation of intensity of received light by said detector which is expressed by a quadratic curve with a variable being the temperature of the reflector mirror of a moisture content calculated therefrom and by then applying the least-squares method to construct a straight line through said quadratic curve.

7. The method of claim 6, wherein said light is laser light.

8. A method of determining the dew point of a gas containing a very small amount of water using an optical dew point meter including a reflector mirror the temperature of which can be varied from room temperature to −80° C. or below, a means for contacting said reflector mirror with the gas to be measured, a means for irradiating said reflector mirror with focused rays of light, and a detector for detecting changes in scattered light or reflected light due to the dew condensed on said reflector mirror, said method comprising the steps of:

contacting said reflector mirror with the gas to be measured;

applying said focused rays of light onto that part of the reflector mirror where it is contacted with said gas;

measuring the intensity of scattered light or reflected light from said reflector mirror;

gradually reducing the temperature of said reflector mirror, either before or while said reflector mirror and said gas contact, thereby condensing dew on said reflector mirror and intermittently measuring a sublimation temperature and a temperature of solidification of superposed layers of said dew;

detecting a change in said measured intensity of said scattered light or reflected light, and measuring a maximum intensity value for said scattered light or a minimum value for said reflected light;

continuously reducing or elevating the temperature of said reflector mirror to obtain a constant intensity of said scattered light or reflected light; and determining the temperature of said reflector mirror at said constant light intensity, said determined reflector mirror temperature corresponding to the dew point.

9. The method of claim 8, wherein said light is laser light.

* * * * *